(12) United States Patent
Abrol et al.

(10) Patent No.: US 10,253,084 B2
(45) Date of Patent: Apr. 9, 2019

(54) METHODS FOR PREDICTING THREE-DIMENSIONAL STRUCTURES FOR ALPHA HELICAL MEMBRANE PROTEINS AND THEIR USE IN DESIGN OF SELECTIVE LIGANDS

(75) Inventors: Ravinder Abrol, Pasadena, CA (US); William A. Goddard, Pasadena, CA (US); Adam R. Griffith, Pasadena, CA (US); Victor Wai Tak Kam, New York, NY (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1694 days.

(21) Appl. No.: 12/142,707

(22) Filed: Jun. 19, 2008

(65) Prior Publication Data

US 2009/0037118 A1 Feb. 5, 2009

Related U.S. Application Data

(60) Provisional application No. 60/936,602, filed on Jun. 21, 2007, provisional application No. 61/072,852, filed on Apr. 3, 2008.

(51) Int. Cl.
*G06F 19/00* (2018.01)
*G01N 33/68* (2006.01)
*C07K 14/705* (2006.01)

(52) U.S. Cl.
CPC ........ *C07K 14/705* (2013.01); *G01N 2500/04* (2013.01)

(58) Field of Classification Search
CPC ................................. G06F 19/16; G06F 19/22
See application file for complete search history.

(56) References Cited

U.S. PATENT DOCUMENTS

| | | |
|---|---|---|
| 2002/0090648 A1 | 7/2002 | Dahiyat et al. |
| 2002/0099506 A1 | 7/2002 | Floriano et al. |
| 2004/0087500 A1 | 5/2004 | Umeyama |
| 2004/0229290 A1 | 11/2004 | Hellinga et al. |
| 2005/0136481 A1 | 6/2005 | Trabanino et al. |
| 2006/0009913 A1* | 1/2006 | Trabanino et al. ............. 702/19 |
| 2006/0100789 A1 | 5/2006 | Itai et al. |
| 2007/0038379 A1 | 2/2007 | Vaidehi |

FOREIGN PATENT DOCUMENTS

WO 2005/052839 6/2005

OTHER PUBLICATIONS

Son et al. Eur Biophys J (1999) 28: 489-498.*
Biggin et al. Biophysical Chemistry 76 (1999) 161-183.*
Hurwitz et al. Phil. Trans. R. Soc. B, 2006, 361,65-475.*
Al-Lazikani, B.; Jung, J.; Xiang, Z. X.; Honig, B. "Protein Structure Prediction" Current Opinion in Chemical Biology 2001, 5(1),51-56.
Altschul, S.F., et at. "Gapped BLAST and PSI-BLAST: a new generation of protein database search programs." *Nucleic Acids Res.* 25, 3389 (1997).
Brooijmans, N.; Kuntz, I. D. "Molecular Recognition and Docking Algorithms", Annual Review of Biophysics and Biomolecular Structure 2003, 32, 335-373.
Chen, c., A. Kernytsky, B. Rost, "Transmembrane helix predictions revisited." *Protein Science*. 11,2774-2791 (2002).
Cherezov, V., et al. (2007). "High-resolution crystal structure of an engineered human 2 adrenergic G protein-coupled receptor". *Science* 318, 1258-1265.
Cho, A. Wendel,J.A., Vaidehi, N., Kekenes-Huskey,P.M., Floriano, W.B., Maiti, P.K., and Goddard III, W.A. (2005) "The MPSim-Dock Hierarchical Docking Algorithm: Application to the eight trypsin Inhibitor co-crystals", J. Compo Chern., 26, 48-71.
DeMaeyer, M.; Desmet, J.; Lasters, I. "All-In-One: a highly detailed rotamer library improves both accuracy and speed in the modeling of sidechains by dead-end elimination", Folding & Design 1997,2(1),53-66.
Deisenhofer J., Epp 0., Miki K., Huber R., and Michel H. 1985. "Structure of the protein subunits in the photosynthetic reaction centre of Rhodospeudomonas viridis at 3 A resolution", *Nature* 318,618-624.
Desjarlais, J. R.; Handel, T. M. "De Novo design of the hydrophobic cores of proteins", Protein Science 1995,4(10),2006-2018.
Deupi, X., et al. "Ser and Thr Residues Modulate the Conformation of Pro-Kinked Transmembrane a-Helices." *Biophysical Journal*. 86, 105-115 (2004).
R. L. Dunbrack Jr. and M. Karplus. "Backbone-dependent Rotamer Library for Proteins: Application to Side-chain prediction." J. Mol. Biol. vol. 230, 543-574 (1993).
Dwyer, M. A.; Looger, L. L.; Hellinga, H. W. "Computational Design of a Biologically Active Enzyme", *Science* 2004, 304(5679), 1967-1971.

(Continued)

*Primary Examiner* — Michael L Borin
(74) *Attorney, Agent, or Firm* — Steinfl + Bruno LLP

(57) ABSTRACT

A method for practical prediction of the three-dimensional structure of α-helical membrane proteins (HMPs) is described. The method allows one to predict the binding site and structure for strongly bound ligands. The method combines a protocol of computational methods enabling a complete ensemble of packings to be sampled and systematically reducing this ensemble to progressively more accurate structures until at the end there remain a few that might be functionally relevant and likely to play a role in all binding and activation processes. This method is well suited to automatic operation making it practical to obtain, for example, the ensemble of important structures for all human GPCRs. With this ensemble of all active GPCR structures in the human body, an infimum method is presented to maximize efficacy toward the selected target while minimizing binding to all other GPCRs to eliminate toxicity arising from cross-reacting with other GPCRs (a most common source of drug failure). This infimum method is broadly applicable to any set of proteins where a ligand is desired to be able to modulate the function of one protein while not affecting the function of other proteins.

29 Claims, 20 Drawing Sheets

Specification includes a Sequence Listing.

(56) References Cited

OTHER PUBLICATIONS

Eisenmenger, F.; Argos, P.; Abagyan, R. "A method to configure protein side-chains from the main-chain trace in homology modeling",Journal of Molecular Biology 1993,231(3), 849-860.
Farrens D.L. et al. (1996) "Requirement of Rigid-Body Motion of Transmembrane Helices for Light Activation of Rhodopsin", Science 274,768-770.
Heo, J., Han, S.K., Vaidehi, N., Wendel, J., Kekenes-Huskey, P., Goddard III, W.A. (2007) Prediction of the 3D Structure of FMRF-amide Neuropeptides Bound to the Mouse MrgCll GPCR and Experimental Validation. Chem. Bio. Chem., 8, 1527-1539.
Holm, L.; Sander, C. "Fast and Simple Monte Carlo Algorithm for Side Chain Optimization in Proteins: Application to Model Building by Homology", Proteins-Structure Function and Genetics 1992, 14(2),213-223.
Jacobson, M. P.; Pincus, D. L.; Rapp, C. S.; Day, T. J. F.; Honig, B.; Shaw, D. E.; Friesner, R. A. "A Hierarchical Approach to All-Protein Loop Prediction", Proteins-Structure Function and Bioinformatics 2004,55(2),351-367.
Katoh, Kuma, Toh, Miyata, "MAFFT version 5: improvement in accuracy of multiple sequence alignment." Nucleic Acids Res. 33, 511 (2005).
Kobilka B. (2007), "G protein coupled receptor structure and activation", Biochimica et Biophysica Acta 1768, 794-807.
Krogh A, Larsson B, von Heijne G, Sonnhammer EL (2001). "Predicting transmembrane protein topology with a hidden Markov model: application to complete genomes". J Mol. Biol. 305,567580.
Kubinyi H., "Drug Research: myths, hype and reality", Nature Reviews Drug Discovery 2, 665-668 (2003).
Kuhlman, B.; Baker, D. "Native protein sequences are close to optimal for their structures", Proceedings of the National Academy of Sciences of the United States of America 2000, 97(19),10383-10388.
Kussell, E.; Shimada, J.; Shakhnovich, E. I. "Excluded Volume in Protein Side-chain Packing", Journal of Molecular Biology 2001, 311(1), 183-193.
Lagerstrom M.C. and Schioth H.B. (2008) "Structural diversity of G protein coupled receptors and significance for drug discovery", Nature Reviews Drug Discovery 7,339-357.
Li, Y., et al. (2007) "Prediction of the 3D Structure and Dynamics of Human DP G-Protein Coupled Receptor Bound to an Agonist and an Antagonist", J. Am. Chem. Soc. 129, 10720-10731.
Looger, L. L.; Hellinga, H. W. "Generalized Dead-end Elimination Algorithms Make Large-scale Protein Side-chain Structure Prediction Tractable: Implications for Protein Design and Structural Genomics", Journal of Molecular Biology 2001,307(1),429-445.
Lovell, S. c.; Word, J. M.; Richardson, J. S.; Richardson, D. C. The Penultimate Rotamer Library, Proteins-Structure Function and Genetics 2000, 40(3),389-408.
MacKerell, Jr. AD, et al. (1998). "All-atom empirical potential for molecular modeling and dynamics studies of proteins", Phys Chern B 102: 3586-3616.
Mayo, S. L.; Olafson, B. D.; Goddard, W. A. "Dreiding: A Generic Force Field for Molecular Simulations", Journal of Physical Chemistry 1990, 94(26), 8897-8909.
Mendes, J.; Baptista, A. M.; Carrondo, M. A.; Soares, C. M. "Improved Modeling of Side-Chains in Proteins With Rotamer-Based Methods:A Flexible Rotamer Model", Proteins-Structure Function and Genetics 1999,37(4),530-543.
Mendes, J.; Soares, C. M.; Carrondo, M. A. "Improvement of side-chain modeling in proteins with the self-contained mean field theory method based on a an analysis of the factors influencing prediction", Biopolymers 1999,50(2), 111-131.
E.C. Meng and H.R. Bourne, "Receptor activation: what does the rhodopsin structure tell us?", Trends Pharmacal. Sci. 22 (2001), 587-593.
Murakami, M., Kouyama, T. (2008) "Crystal structure of squid rhodopsin", Nature 453, 363-367.
Palczewski, K., et al. (2000) "Crystal structure of rhodopsin: A G protein-coupled receptor", Sci. 289, 739-745.

Peterson, R. W.; Dutton, P. L.; Wand, A. J. "Improved side-chain prediction accuracy using an ab initio potential energy function and a very large rotamer library", Protein Science 2004,13(3), 735-751.
Ponder, J. W.; Richards, F. M. "Tertiary Templates for Proteins", Journal of Molecular Biology 1987, 193(4),775-791.
W. Rocchia, E. Alexov and B. Honig, "Extending the applicability of the nonlinear Poisson-Boltzmann equation: Multiple dielectric constants and multivalent ions", J. Phys. Chern. BIOS (2001) 6507-6514.
Schertler, G.F. (1998) "Structure of rhodopsin", Eye, 12,504-510.
Sgourakis. N. et al. "A Method for the Prediction for GPCRs Coupling Specificity to G-proteins Using Refined Profile Hidden Markov Models", BMC Bioinformatics, Apr. 2005, vol. 6, pp. 1-12.
Thompson, J., D. Higgins, T. Gibson, "CLUSTAL W: improving the sensitivity of progressive multiple sequence alignment through sequence weighting, position-specific gap penalties and weight matrix choice." Nucleic Acids Res. 22, 4673 (1994).
Gabor Tusnady and Istvan Simon, "The HMMTOP transmembrane topology prediction server." Bioinformatics. 17 (9), 849-850 (2001).
Vaidehi, N., Schlyer, S. Trabanino, R. J., Floriano, W.B., Abrol, R, et al. (2006)."Predictions of CCR1 chemokine receptor structure and BX 471 antagonist binding followed by experimental validation", J. Biol. Chem. 281, 27613-27620.
Wernisch, L.; Hery, S.; Wodak, S. J. "Automatic protein design with all atom force fields by exact and heuristic optimization", Journal of Molecular Biology 2000, 301(3), 713-736.
Wimley WC, Creamer TP & White SH (1996). "Solvation energies of amino acid side chains and backbone in a family of host-guest pentapeptides", Biochemistry 35, 5109-5124.
Xiang, Z. X.; Honig, B. "Extending the accuracy limits of prediction for side-chain conformations", Journal of Molecular Biology 2001, 311(2), 421-430.
PCT Search Report for PCT/US2008/067553 in the name of California Institute of Technology filed on Jun. 19, 2008.
PCT Written Opinion for PCT/US2008/067553 in the name of California Institute of Technology filed on Jun. 19, 2008.
Bray JK and Goddard WA. The structure of human serotonin 2c G-protein-coupled receptor bound to agonists and antagonists. J. Mol. Graph. Model. 27, 66-81 (2008).
Fanelli F and De Benedetti PG. Computational Modeling Approaches to Structure-Function Analysis of G-Protein-Coupled Receptors. Chem. Rev. 105, 3297-3351 (2005).
Floriano, W.B., Vaidehi, N., Singer, M., Shepherd, G., Goddard III, W.A. (2000) Molecular mechanisms underlying differential odor responses of a mouse olfactory receptor, Proc. Natl Acad. Sci U.S.A. 97, 10712-10716.
Freddolino PL, et al. Structure and function prediction for human β2-adrenergic receptor. Proc. Natl. Acad. Sci. USA, 101, 2736-2741 (2004).
Goddard WA and Abrol R. 3D Structures of G-Protein Coupled Receptors and Binding Sites of Agonists and Antagonists. Journal of Nutrition 137, 1528S-1538S (2007).
Huang, Shoichet, and Irwin. Benchmarking sets for molecular docking. J. Med. Chem. 49, 6789-6801 (2006).
Kalani MY, et al. The predicted 3D structure of the human D2 dopamine receptor and the binding site and binding affinities for agonists and antagonists. Proc. Natl. Acad. Sci. USA, 101, 3815-3820 (2004).
Kam VWT and Goddard WA. Flat-Bottom Strategy for Improved Accuracy in Protein Side-Chain Placements. J. Chem. Theory Comput. 4, 2160-2169 (2008).
Li YY, Zhu FQ, Vaidehi N, and Goddard WA. Prediction of the 3D Structure and Dynamics of Human DP G-Protein Coupled Receptor Bound to an Agonist and an Antagonist. J. Am. Chem. Soc. 129, 10720-10731 (2007).
Mayo, S. L., Olafson, B.D. Goddard III, W.A. DREIDING—a generic force field for molecular simulations. J. Phys. Chem. 94, 8897-8909 (1990).
Moustakas DT, et al. Development and validation of a modular, extensible docking program: DOCK 5. J. Comput. Aided Mol. Design 20, 601-619 (2006).

(56) References Cited

OTHER PUBLICATIONS

Peng JYP, et al. The Predicted 3D Structures of the Human M1 Muscarinic Acetylcholine Receptor with Agonist or Antagonist Bound. *ChemMedChem* 1, 878-890 (2006).
Vaidehi N, et al. Prediction of Structure and Function of GPCRs. *Proc. Natl. Acad. Sci., USA* 99, 12622-12627 (2002).
Warren GL, et al. A critical assessment of docking programs and scoring functions. *J. Med. Chem.* 49, 5912-5931 (2006).
Katoh, K., et al., MAFFT: a novel method for rapid multiple sequence alignment based on fast Fourier transform, Nucleic Acids Res. 2002, 30: 3059-3066.
Katoh, K., et al., PartTree: an algorithm to build an approximate tree from a large number of unaligned sequences, Bioinformatics 2007, 23: 372-374.
Katoh, K., et al., Recent developments in the MAFFT multiple sequence alignment program, Briefings in Bioinformatics 2008, 9: 286-298.
White SH., et al., Membrane Protein Folding and Stability: Physical Principles, Annu. Rev. Biophys. Biomol. Struc. 1999, 28: 319-365.
Kernystky, A., et al., Static benchmarking of membrane helix predictions, Nucleic Acids Res. 2003, 31: 3642-3644.
Desjarlais, J. R., et al., De Novo design of the hydrophobic cores of proteins, Protein Science 1995, 4: 2006-2018.
Popot, J., et al., Membrane Protein Folding and Oligomerization: The Two-Stage Model, Biochemistry 1990, 29: 4031-4037.
Lomize, A., et al., Quantification of helix-helix binding affinities in micelles and lipid bilayers, Protein Science 2004, 13: 2600-2612.
White, S., The progress of membrane protein structure determination, Protein Science 2004, 13: 1948-1949.
Orientations of Proteins in Membranes (OPM) database, http://opm.phar.umich.edu retrieved May 27, 2011.
UCSF Dock 6.5 Website, http://dock.compbio.ucsf.edu/index retrieved Jan. 13, 2012.
HMMTOP Prediction of transmembrane helices and topology of proteins, Version 2.0 website, http://www.enzim.hu/hmmtop/ retrieved Jan. 13, 2012.
Kobayashi, T. et al. Amino Acid Residues Conferring Ligand Binding Properties of Prostaglandin I and Prostaglandin D Receptors, J. Biol Chem. vol. 275, No. 32, 24294-24303, (2000).
Kobilka, B., Deupi, X. "Conformational complexity of G Protein Coupled Receptors." *Trends in Pharmacological Sciences* 2007 28:397-406.
BLAST web-based wrapper program, http://www.expasy.org/tools/blast retrieved Jan. 18, 2012.
Restriction Requirement issued for U.S. Appl. No. 12/944,692, filed Nov. 11, 2010, in the name of William A. Goddard et al. dated Dec. 21, 2011.
Restriction Requirement dated Apr. 16, 2012 for U.S. Appl. No. 12/944,692, filed Nov. 11, 2010 in the name of William A. Goddard III.
Non-Final Office Action dated Aug. 15, 2012 for U.S. Appl. No. 12/944,692, filed Nov. 11, 2010 in the name of William A. Goddard III.
Final Office Action dated Feb. 4, 2012 for U.S. Appl. No. 12/944,692, filed Nov. 11, 2010 in the name of William A. Goddard III.
Non-Final Office Action dated Jul. 24, 2014 for U.S. Appl. No. 12/944,692, filed Nov. 11, 2010 in the name of William A. Goddard III.
Restriction Requirement dated Feb. 22, 2012 for U.S. Appl. No. 12/944,700, filed Nov. 11, 2010 in the name of William A. Goddard III.
Final Office Action dated Dec. 17, 2012 for U.S. Appl. No. 12/944,700, filed Nov. 11, 2010 in the name of William A. Goddard III.
Non-Final Office Action dated Aug. 6, 2014 for U.S. Appl. No. 12/944,700, filed Nov. 11, 2010 in the name of William A. Goddard III.
Non-Final Office Action dated May 10, 2012 for U.S. Appl. No. 12/944,700, filed Nov. 11, 2010 in the name of William A. Goddard III.
Final Office Action dated Dec. 23, 2014 for U.S. Appl. No. 12/944,700, filed Nov. 11, 2010 in the name of William A. Goddard III.
Bray, J.K. "The Development and Application of Computational Methods for the Prediction of G Protein-Coupled Receptor Structures" California Institute of Technology, Pasadena, CA defended Aug. 10, 2009 (published 2010).
Final Office Action dated Feb. 9, 2015 for U.S. Appl. No. 12/944,692, filed Nov. 11, 2010 in the name of William A. Goddard III.

\* cited by examiner

```
D1  VQLSWHKAKPTS--------------PSDGNATSLAETIDNCDSSLSRTYAISSSVISFY
D5  VQLNWHRDQAASWGGLDLPNNLANWTPWEEDFWEPDVNAENCDSSLNRTYAISSSLISFY
D2  LFG-----------------------LNN---ADQNECIIANPAFVVYSSIVSFY
D3  LFG-----------------------FNTT--GDPTVCSISNPDFVIYSSVVSFY
D4  LCG-----------------------LNDVRGRDPAVCRLEDRDYVVYSSVGSFE

D1  IPVAIMIVTYTRIYRIAQKQ--IRRIAALERAAVHAKNCQTTTGNGKPVECSQPESSFKM
D5  IPVAIMIVTYTRIYRIAQVQ--IRRISSLERAAEHAQSCRSS------AACAPDTSLRA
D2  VPFIVTLLVYIKIYIVLR----RRRKRVN---TKRSSRAFRAHLRAPLKGNCTHPEDMKL
D3  LPFGVTVLVYARIYVVLKQ---RRRKRIL---TRQNSQCNSVRPGFPQQTLSPDPAHLEL
D4  LPCPLMLLLYWATFRGLQRWEVARRAKLHGRAPRRPSGPGPPSPTPPAPRLPQDPCGPDC

D1  SFKRETKVLKTLSVIMGVFVCCWLPFFILNCILPFCGSGETQP----FCIDSNTFDVFVW
D5  SIKKETKVLKTLSVIMGVFVCCWLPFFILNCMVPFCSGHPEGPPAGFPCVSETTFDVFVW
D2  CTVIMKSNGSFPVNRRRVEAARRAQELEMEMLSSTSPPERTRYSPIPPSHHQLTLPDPSH
D3  -------KRYYSICQDTALGGPGFQERGGELKR----EEKTRNSLSPTIAPKLSL-----
D4  APP-APGLPRGPCGPDCAPAAPGLPPDPCGPDCAPPAPGLPQDPCGPDCAPPAPGLPRGP

D1  FGWANSSLNPIIYAFNADFRKAFSTLLGCYRLCPATNNAIETVSINNNGAAMFSS-----
D5  FGWANSSLNPVIYAFNADFQKVFAQLLGCSHFCSRT--PVETVNISN---ELISY-----
D2  HGLHSTPDSPAKPEKNGHAKDHPKIAKIFEIQTMPNGKTRTSLKTMSRR-KLSQQ-----
D3  -------------------------EVRKLSNGRLSTSLKLGPLQPRGVPL-----
D4  CGPDCAPPAPGLPQDPCGPDCAPPAPGLPPDPCGSNCAPPDAVRAAALPPQTPPQTRRRR

D1  ---------HHEPRGSISKECNLVYLIPHAVGS-SEDLKKEEAAG-------IARPLEKL
D5  ---------NQDIVFHKEIAAAYIHMMPNAVTPGNREVDNDEEEGPFDRMFQIYQTSPDG
D2  -------KEKKATQMLAIVLGVFIICWLPFFITHILNIHCD-CNIPPVLYSAFTWLGYVNS
D3  -------REKKATQMVAIVLGAFIVCWLPFFLTHVLNTHCQTCHVSPELYSATTWLGYVNS
D4  RAKITGRERKAMRVLPVVVGAFLLCWTPFFVHITQALCPACSVPPRLVSAVTWLGYVNS

D1  SPALSVILDYDTD--VSLEKIQPITQNGQHPT
D5  DPVAESVWELDCEGEISLDKITPFTPNGFH--
D2  AVNPIIYTTFNIEFRKAFLKILHC--------
D3  ALNPVIYTTFNIEFRKAFLKILSC--------
D4  ALNPVIYTVFNAEFRNVFRKALRACC------
```

FIG. 5

|  | Beta2 | | Bovine Rhodopsin | |
|---|---|---|---|---|
|  | RMSD | Energy | RMSD | Energy |
| TM1 | 0.78 | 0.86 | 0.82 | 0.70 |
| TM2 | 1.07 | 1.52 | 2.02 | 1.81 |
| TM3 | 1.14 | 1.34 | 0.98 | 1.18 |
| TM4 | 0.63 | 0.64 | 1.24 | 0.93 |
| TM5 | 1.61 | 1.95 | 1.62 | 1.45 |
| TM6 | 1.55 | 1.37 | 1.00 | 0.79 |
| TM7 | 1.95 | 2.05 | 1.77 | 1.89 |
| Min | 0.63 | 0.64 | 0.82 | 0.70 |
| Max | 1.95 | 2.05 | 2.02 | 1.89 |
| Avg | 1.25 | 1.39 | 1.35 | 1.25 |

FIG. 13

| Structure | TotalE |
|---|---|
| 0_0_0_0_0_330_0 | -237 |
| 0_0_0_0_300_330_0 | -234 |
| 0_0_0_0_180_330_0 | -231 |
| 0_0_0_0_90_330_0 | -220 |
| 0_0_0_0_210_330_0 | -215 |
| 0_0_0_0_60_330_0 | -213 |
| 0_0_0_0_0_0_0 | -210 |
| 0_0_0_0_330_330_0 | -203 |
| 0_0_0_0_90_0_0 | -195 |
| 0_0_0_0_180_0_0 | -189 |
| 0_0_0_0_60_0_0 | -175 |

$$\Delta G_{solvation} = \Delta G_{elec} + \Delta G_{vdw} + \Delta G_{cav}$$

$$\Delta G_{vdw} = \Delta G_{rep} + \Delta G_{disp}$$

$$\Delta G_{cav} = \Delta G_{antipressure} + \Delta G_{entropic}$$

$$\Delta G_{vdw} + \Delta G_{cav} = \gamma S + b$$

$S =$ Solvent Accessible Surface Area $\gamma, b =$ Parameters derived from experiment $$VDW_{flat}(r) = \begin{cases} VDW(r) & r > R_e \\ D_e & R_e - \Delta < r < R_e \\ VDW(r + \Delta) & r < R_e - \Delta \end{cases}$$

| Diversity | Starting | 0.2Å | 0.6Å | 1.0Å | 1.4Å | 1.8Å | 2.2Å | 3.0Å | 5.0Å | All-Torsion |
|---|---|---|---|---|---|---|---|---|---|---|
| Rotamer Count | 35828 | 14755 | 3195 | 1014 | 378 | 214 | 136 | 84 | 44 | 382 |

| Rotamer Library | Optimal Scaling Factor s for core residues | Optimal Scaling Factor s for surface residues | Core residue RMSD (Å) for optimal s | Surface residue RMSD (Å) for optimal s |
|---|---|---|---|---|
| 0.2Å | 1.4 | 0.6 | 0.309 | 0.939 |
| 0.6Å | 1.2 | 0.8 | 0.414 | 1.010 |
| 1.0Å | 1.2 | 0.9 | 0.515 | 1.107 |
| 1.4Å | 1.3 | 0.8 | 0.605 | 1.171 |
| 1.8Å | 1.2 | 0.7 | 0.742 | 1.227 |
| 2.2Å | 0.8 | 0.6 | 1.105 | 1.371 |
| 3.0Å | 0.7 | 0.6 | 1.439 | 1.625 |
| 5.0Å | 0.7 | 0.7 | 1.835 | 1.935 |
| All-Torsion | 0.9 | 0.8 | 0.656 | 1.224 |

METHODS FOR PREDICTING THREE-DIMENSIONAL STRUCTURES FOR ALPHA HELICAL MEMBRANE PROTEINS AND THEIR USE IN DESIGN OF SELECTIVE LIGANDS

CROSS REFERENCE TO RELATED APPLICATIONS

This application claims priority to U.S. Provisional Application 60/936,602 filed on Jun. 21, 2007, for "3D Structures and Dynamics of Agonists and Antagonists Bound to G-protein Coupled Receptors" by William A. Goddard, and to U.S. Provisional Application 61/072,852 filed on Apr. 3, 2008 for "GEnSeMBLE: GPCR Ensemble of Structures in Membrane Bilayer Environment" by Ravinder Abrol, Adam R. Griffith and William A. Goddard, the contents of both of which are incorporated herein by reference in their entirety.

STATEMENT OF GOVERNMENT INTEREST

The U.S. Government has certain rights in this invention pursuant to Grant No. R21-MH073910-01-A1 awarded by the National Institutes of Health.

FIELD

The present disclosure relates to α-helical membrane proteins (HMPs) In particular, it relates to methods for predicting three-dimensional structures for HMPs and their use in designing selective HMPs ligands.

BACKGROUND

α-helical membrane proteins (HMPs) comprise the largest subfamily of integral membrane proteins which make up for about 30% of the eukaryotic genome [1]. HMPs proteins exhibit one or more α-helices (also called transmembrane helices or TM helices) that span the cellular membrane and play important roles in a variety of cellular processes like signal transduction, transport of ions or molecules across membranes, metabolism, cell-cell communication. Some of the members include bacteriorhodopsin, cytochrome c oxidases, voltage-gated ion channels, aquaporins, and G protein-coupled receptors (GPCRs).

The HMP family is dominated by proteins with 7 TM α-helices called 7TM proteins. The GPCRs which also contain 7 TM α-helices makeup for the majority of the 7TM proteins, as a small number of 7TM proteins do not couple to G proteins. The 7TM proteins are activated by a variety of bioactive molecules, like biogenic amines, peptides, lipids, nucleotides, proteins, tastants, odorants and non-molecular sensory signals like light, touch etc [2], making them essential for a range of physiological processes (e.g. neurotransmission, cellular metabolism, secretion, cell growth, immune defense, and differentiation). They are also the largest family in human genome with about 800 7TM proteins identified, including about more than 400 non-sensory receptors organized into 5 families (GRAFS): Glutamate, Rhodopsin, Adhesion, Frizzled/Taste2, and Secretin [3]. Due to their mediation of numerous critical physiological functions, 7TM proteins are implicated in all major disease areas including cardiovascular, metabolic, neurodegenerative, psychiatric, cancer and infectious diseases. Indeed these proteins represent 30-50% of the current drug targets for activation (by agonists) or inhibition (by antagonists).

Other members of the HMP family are also involved in a range of critical functions like photosynthesis, proton transport (Bacteriorhodopsin), electron transfer in enzymatic reactions (Cytochrome c oxidase), transport of critical substrates across membranes (ABC transporters), translocation of other membrane proteins during/after their synthesis (SecY), voltage-gated ion channels (potassium channels), and water transport across membranes (aquaporins) to name a few.

Biochemical and biophysical studies of HMPs have accelerated progress in identifying various subtypes with specific cell and tissue functions. However, progress in developing new targeting compounds that can be used to selectively modulate the functions of HMPs to obtain a biological activity of interest (e.g. new drugs with reduced toxicity and side effects) has been severely hampered by the lack of 3D structures for nearly all human HMPs.

This lack of 3D structures of HMP has motivated extensive efforts and huge levels of funding around the world to determine the structures using protein crystallography, but currently there are accurate experimental structures for only about 120 HMPs and for only one human 7TM protein of the 800. The first experimental 3D structure for any membrane protein (MP) was published in 1985 [4] for the photosynthetic reaction center. Since then experimental structures have been obtained for only about 160 unique MPs, of which only 10 are human. For 7TM proteins (a particularly challenging class of MPs) of any form of life, the first structure was determined in 2000 for bovine rhodopsin [5], the second structure was determined in 2007 for a modified human β2 adrenergic receptor [6], and the third structure was determined in 2008 for squid rhodopsin [7]. Thus of the 800 human 7TM structures needed for drug optimization, just one structure is known experimentally and obtaining all others is destined to require decades and huge additional funding.

Moreover, since crystallographic observation requires that all molecules in the crystal have the same conformation, the few 7TM structures observed so far have been modified to prohibit flexibility and/or binding a ligand that locks in a specific conformation. This is a significant limitation of the crystallographic approach, since it is well established that the process of activating a 7TM protein involves a sequence of conformational changes that enable the cell to convert extracellular signals into physiological responses [8].

Current experimental methods provide not even the promise of ever enabling resolution of the dynamical structures through which the 7TM protein evolves during activation. This provides an even more significant limitation in the experimental study of the 7TM proteins since it is expected that different types of 7TM ligands, such as agonists, antagonists, inverse agonists, and modulators may bind to different receptor conformations, and that some 7TM proteins may act as dimers or multimers.

An alternative to experimental determination of 3D structures is the use of homology computational methods. Here one aligns the amino acid sequence of the unknown with that of one or more known structures, accounting for various non-alignable parts (gaps and bulges) to build the structure for the unknown using the known as a guide. To obtain a sufficiently accurate structure for ligand design (where ligand can be a drug) aimed at altering the function of HMPs, homology computational methods generally require comparison to a number of related experimental structures, ideally with a sequence identity well over 40%. In contrast, there are only three structures for 7TMs and the sequence identity desirable to provide predicted structures suitable for applications such as drug design is significantly higher than the sequence identify detectable by this approach alone. In a further approach illustrated by PCT patent publication WO/2005/17805, incorporated herein by reference in its entirety, a "MembStruk" method is used for predicting a single low-energy structure for a multipass TM protein.

SUMMARY

Methods and systems are herein disclosed that allow practical determination of the three dimensional structure of HMPs, including but not limited to human and animals HMPs. Methods and systems are also herein disclosed that allow design of a HMP ligand that is able to elicit a biological activity of interest, including the biological activities required for treatment of a disease, through selective binding of target HMPs and in particular of 7TM proteins.

According to a first aspect, a method for predicting structures of an α-helical membrane protein (HMP), is disclosed, the α-helical membrane protein including M α helices, M being an integer greater than or equal to 2. The method comprises: predicting transmembrane (TM) sequences of the HMPs; constructing individual TM helices of the HMPs; sampling multiple conformations of HMPs; and generating multiple rotational combinations, to provide an ensemble of multiple energy structures associated to binding of the HMPs with corresponding HMP ligands.

According to a second aspect, a method for predicting structures of an α-helical membrane protein (HMP), is disclosed, the α-helical membrane protein including M α helices, M being an integer greater than or equal to 2. The method comprises: predicting transmembrane (TM) amino acid sequences of the HMP; constructing individual TM helical structures of the HMP based on said predicted TM amino acid sequences; and defining a set of candidate M-helix bundle conformations, each conformation comprising constructed individual TM helical structures. The method also comprises: partitioning interactions between the constructed individual TM helical structures of the M-helix bundle into (M−N)-helix interactions, N being an integer, in the range of 1≤N≤M−2, each (M−N)-helix interaction having a (M−N)-helix energy. The method further comprises: based on (M−N)-helix energies, estimating interaction energies of the defined set of candidate M-helix bundle conformations; based on the estimated interaction energies of the defined set, selecting a first subset of conformations for binding of the HMP to HMP ligands suitable to bind to the HMP; and assembling an M-helix bundle for each conformation of said first subset of conformations. The method still further comprises: for each said conformation evaluating interaction energies among all M helices; based on the evaluated interaction energies among all M helices, selecting a second subset of conformations, said second subset being a subset of the first subset; and identifying relevant HMP structures based upon binding of ligands to said second subset of conformations.

According to a third aspect, a method for designing a ligand capable of exerting a biological activity through selective binding to a target α-helical membrane protein (HMP) over an anti-target HMP, is disclosed, the α-helical membrane protein including M α helices. The method comprises: and identifying the target HMP associated with the biological activity; and identifying the anti-target HMP. The method further comprises: predicting a structure of the target HMP suitable for complexing with target-HMP candidate ligands and predicting a structure of the anti-target HMP suitable for complexing with anti-target-HMP candidate ligands. The method also comprises optimizing the structure of the candidate ligand to maximize binding of said ligand compound with the target HMP and minimize binding of said ligand with the anti-target HMP, thus providing an optimized ligand; and verifying the ability of the optimized ligand to exert the biological activity.

According to a fourth aspect, a method for predicting transmembrane (TM) sequences of an α-helical membrane protein (HMP) is disclosed, the method comprising: predicting said TM sequences based on hydrophobicity of said TM sequences to generate a hydrophobicity profile, wherein hydrophobic portions of the hydrophobicity profile correspond to TM helices.

Further embodiments of the present disclosure are provided in the written specification, drawings and claims.

In accordance with the embodiments of the present disclosure, practical determination of different conformations of virtually all HMPs of living organisms, including humans and animals can be enabled, In particular, identification of low-energy conformations of HMPs can be performed with the methods and systems herein disclosed, which can be used to identify three dimensional structures of HMPs associated with biological activities and corresponding ligands able to trigger such activities through selective HMP binding.

In particular, the identification of the ensemble of all active HMP structures in a living organism can be utilized, to design a HMP ligand with maximized binding affinity toward the selected target HMP(s) and minimized binding affinity to all other HMPs. The ligand so designed can be used to selectively elicit a biological activity of interest in the living organism and to eliminate unwanted biological activities usually associated with triggering said biological activity of interest in said organism.

The methods and systems herein disclosed can therefore have a wide range of applications in fields such as microbiology and biochemistry, but also farm industry and pharmacology. In particular, the methods and systems herein disclosed can be used to design a drug able to treat a disease by eliciting the biological activities associated with a target HMP while minimizing the biological activities associated with anti-target HMPs and toxicity/side effects which follow administration of compounds that cross-react with other HMPs (a most common source of drug failure in GPCRs).

BRIEF DESCRIPTION OF THE DRAWINGS

FIG. 5 shows performing multiple sequences alignment according to an embodiment of the present disclosure illustrated by showing sequences from the five human dopamine receptors D1 to D5 which include the sequences identified in the enclosed sequence listing from SEQ ID NO: 1 to SEQ ID NO: 30.

FIG. 13 shows the performance of the algorithm of FIG. 12, according to an embodiment of the present disclosure.

FIG. 23 shows an accuracy comparison in single sidechain placements according to an embodiment of the present disclosure.

DETAILED DESCRIPTION

Methods and systems are disclosed for predicting three dimensional (3D) structures of HMPs, and, if the HMP is associated with a biological activity in a living organism, also for designing a HMP ligand capable of selectively eliciting said biological activity.

In some embodiments, the 3D structures for the various HMPs are predicted using a method herein also identified as the EnSeMBLE (Ensemble of Structures in Membrane BiLayer Environment) method, which allows to predict 3D structures of HMPs and without using homology to known 3D structures. In particular, accordance with the present disclosure, EnSeMBLE allows to predict the ensemble of low-energy (and therefore highly stable) conformational states of an HMP. As illustrated below more in details, the EnSeMBLE approach has been validated for both Bovine Rhodopsin and Human β2 Adrenergic Receptor, two HMPs for which a high resolution experimental crystal structure is available.

Figure 1:
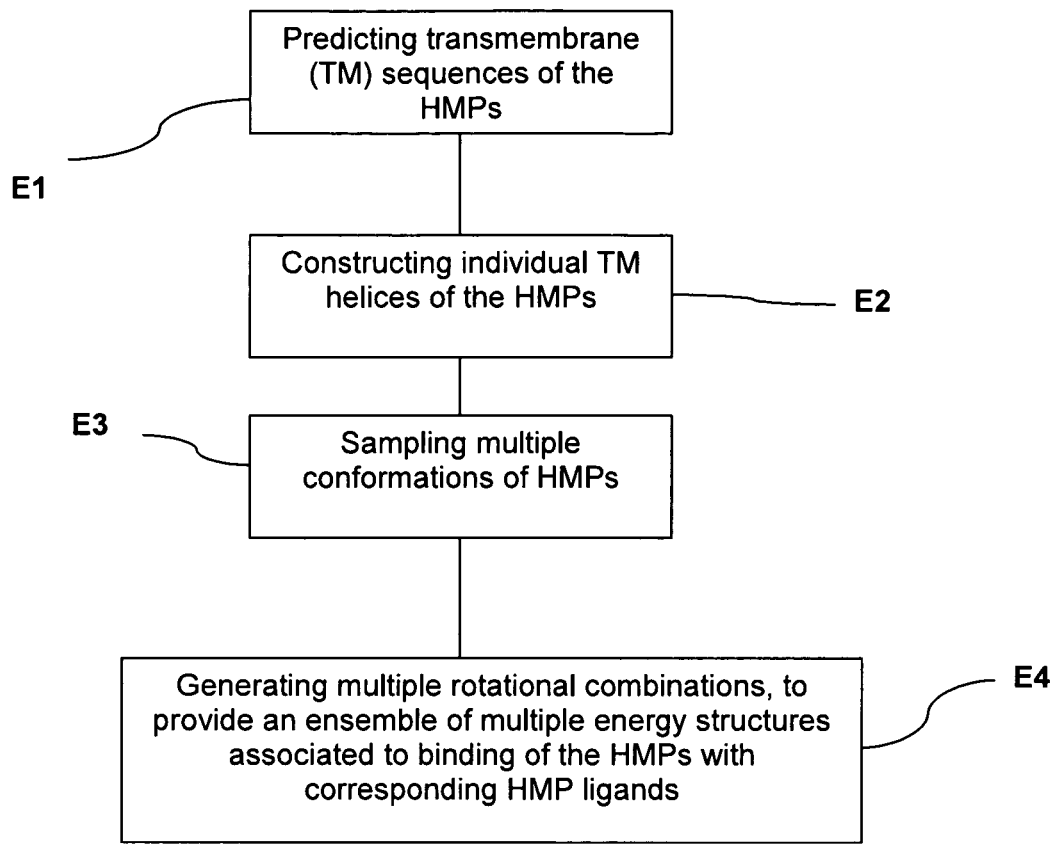
FIG. 1 shows the overall algorithm in accordance with an embodiment of the present disclosure.

The EnSeMBLE method comprises: predicting transmembrane (TM) sequences of the HMPs; constructing individual TM helices of the HMPs; sampling multiple conformations of HMPs; and generating multiple rotational combinations, to provide an ensemble of multiple energy structures associated to binding of the HMPs with corresponding HMP ligands. An embodiment of EnSeMBLE is shown in FIG. 1, wherein the above operations are indicated as (E1), (E2), (E3) and (E4) respectively.

The wording "conformational state" or conformation" as used herein with reference to a helix or a bundle of helices indicates a set of relative rotation angles of a helix in a bundle, the relative rotation of the helix about its axis, the set of relative rotations determining the Cartesian coordinates of the protein backbone atoms in the bundle The wording "rotational combinations" as used herein with reference to a helix or a bundle of helices indicates any possible bundle conformations given an allowed set of rotation angles for each helix in the bundle The term "structure" as used herein with reference to HMP including helices in a bundle and possibly side chains indicates a Cartesian coordinate description for each atom of the HMP in the bundle, including the side chains if any.

Figure 2:
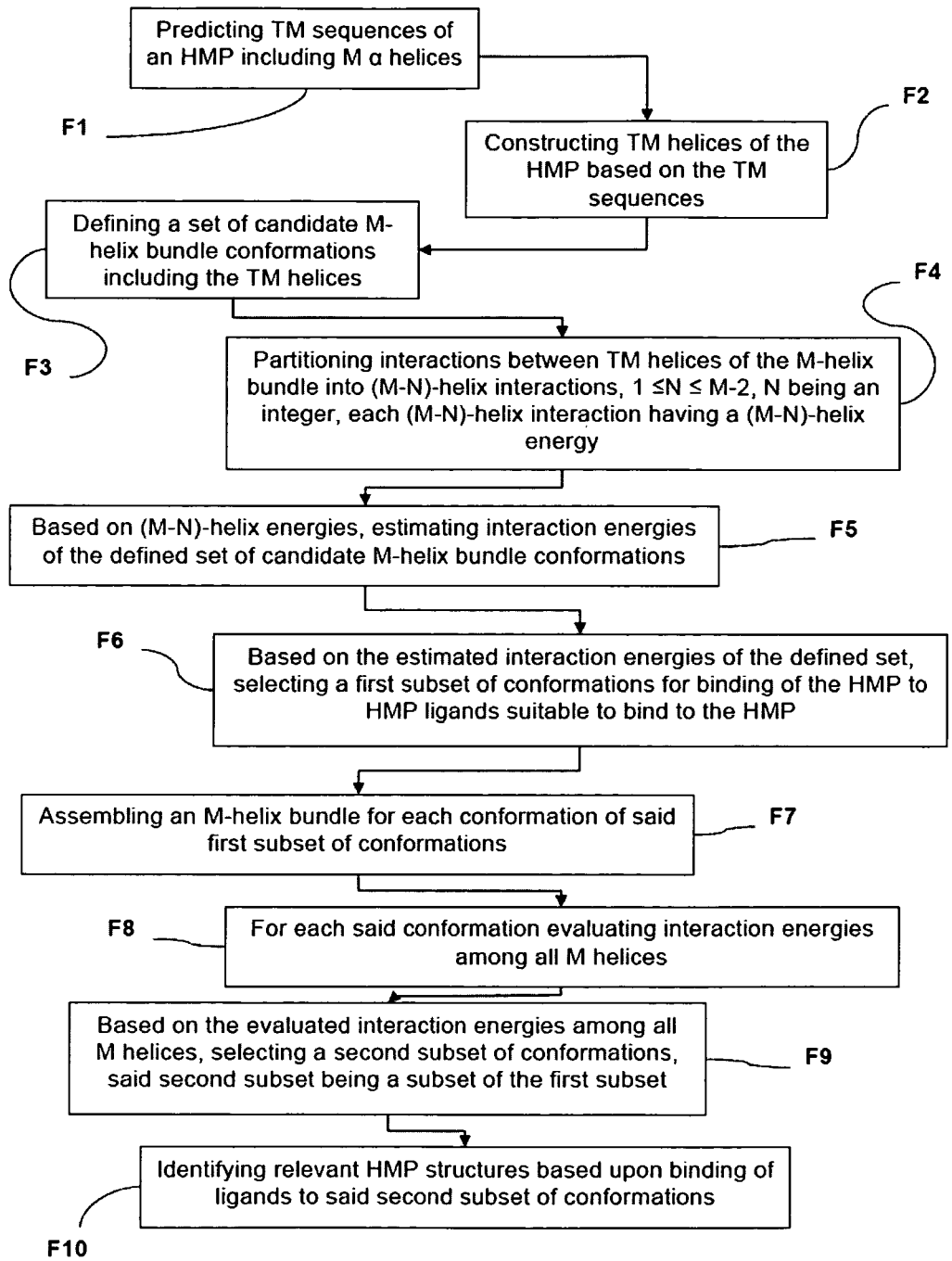
FIG. 2 shows the overall algorithm in accordance with an embodiment of the present disclosure.

An embodiment of EnSeMBLE is shown in FIG. 2. In the illustration of FIG. 2 following the prediction the TM sequences (F1) and the construction of individual TM helices (F2) candidate bundle conformations of the helices are defined (F3) to allow sampling. The sampling is then performed by partitioning interactions between the helices in the defined bundle conformations (F4), and estimating the interaction energies of the helices in the bundle conformations (F5). Generating multiple rotational combinations to provide HMP structures associated to HMP binding with corresponding ligand is then performed by: selecting, based on the interaction energies estimated with (F5), a first subset of HMP conformations that bind to corresponding ligands, (F6), assembling helices into a bundle for each conformation of the first subset (F7), evaluating the interaction energy among the helices in the bundle (F8) selecting, based on the interaction energies estimated with (F8), a second subset of HMP conformations (F9) and identifying the HMP structure based upon binding of ligand to the second subset of conformations (F10).

Figure 3:
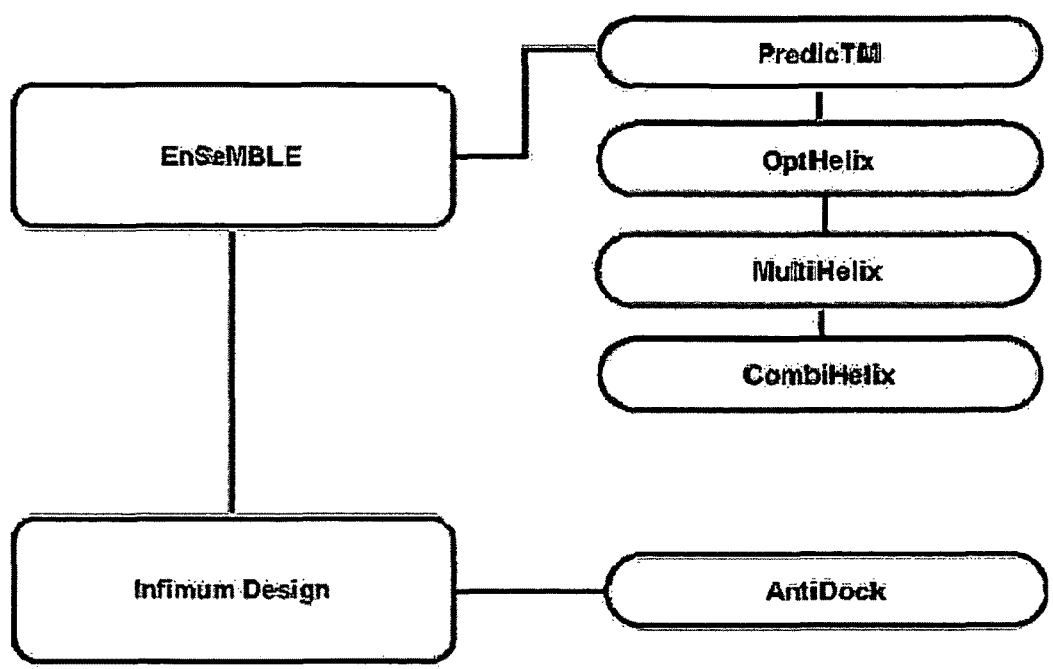
FIG. 3 shows the overall algorithm in accordance with another embodiment of the present disclosure.

In some embodiments, the EnSeMBLE method can be performed by the sequence of algorithms, illustrated in FIG. 3, In those embodiments, predicting transmembrane sequences of the HMPs is performed by the PredicTM algorithm a method to predict the transmembrane (TM) sequences or regions for a membrane protein directly from the hydrophobic properties of each amino acid and the comparison of the particular sequence relative to the sequences of other amino acids, without reference to any other known structures (referred to as ab initio)

Optimization of the individual TM helices so identified is then performed to account for the deviations of some transmembrane domains from the standard alpha helical structure, such as the ones caused by the presence of prolines or glycines in the TM region, sometimes in association with Ser or Thr residues. In particular, in the EnSeMBLE embodiments illustrated in FIG. 3, the structures of the individual TM helices of the HMPs are optimized using OptHelix algorithm, an ab initio approach (no use of known structures) in which molecular dynamics is used to generate relaxed helices with their natural kinks.

Sampling multiple conformations of HMPs is then performed, in particular by sampling a set of M-helix candidate bundle conformations for each HMP. This sampling operation ensures that all combinations of the individual TM helices in an M-helix bundle are examined, without individually evaluating each of those combinations. To ensure that all possible combinations of the M TM helices in the M-helix bundle are evaluated, a full rotation of each helix by $2\pi/N$ radians should be considered, which leads to $N^M$ possible combinations. One implementation can be for $M=7$ (7TM proteins) and $N=12$, which would yield $12^7=35$ million configurations. Other implementations might use $N=24$ or 36 or 72, although $N=12$ results are adequate in a significant number of cases. However, only a few (such as about 10 low energy structures) structures important for the function (effect of ligand binding on function) of HMPs are expected. Accordingly, in the EnSeMBLE method the evaluation of the HMP conformations is performed by multi-helical sampling.

In particular, in some embodiments illustrated in FIG. 3 a multiple-helix sampling of a combinatorially complete set of 7-helix bundle conformations using the MultiHelix algorithm: A sampling algorithm to sample multiple conformations of a HMP and in particular of 7M proteins, which partitions the combinatorial problem $N7$ problem into about 12 $N2$ problems. Thus with $N=12$, 144 combinations of helix' pairs are examined for each of the twelve most important pairs (1-2, 1-7, 2-3, 2-4, 2-7, 3-4, . . . etc) with the SCREAM algorithm (see Appendix A which forms part of the present specification) for side-chain optimization to ensure the optimum interactions between the helices.

The interaction energies of the sampled conformation is then estimated to select a number of conformations adapted to be relevant in binding of the HMPs with corresponding ligands, and identify a number of M-helix bundle conformations for such binding. In particular, in order to estimate the energies of the HMP conformations ($N7=35$ million conformations for 7TM proteins with $N=12$), embodiment also illustrated in FIG. 3, the CombiHelix algorithm is used: This algorithm, that in the example of the 7M proteins, estimates the energy of each of the $N7$ conformations as a sum over the 12 different important pairs of interactions using the results from the MultiHelix step. Based on this combination of bihelical interaction energies a modest number of the lower lying configurations (e.g., 1000 instead of 35 million) is selected (referred to as first subset), which are used to construct explicit 7-helical bundles, with optimized side-chains (e.g., by using the SCREAM algorithm). Here, the Applicants have evaluated the total energy of the optimized 7-helix bundle including all interactions between the helices and also evaluated the interaction with the membrane and solvent using an implicit membrane solvation method (see also below). From these, about 1000 conformations with explicit 7-helix energies, Applicants pick a significantly lower number (e.g., about 10), (referred to as the second set) as the ensemble of low-energy structures for use in docking of agonists, antagonists and inverse agonists. Applicants expect that this will provide a complete set of ligand bound conformations, to understand HMP function. In a case where one might have used, e.g., $N=12$ for the MultiHelix analysis, after finding about best 10 packings, one might consider variations from these structures using angle changes corresponding to $N=24$ or 36 or 72, but only near the optimum predicted structures. This can provide improved resolution of the packing angles.

In the exemplary representation of FIG. 3, EnSeMBLE is shown in connection with a specific embodiment of the method to design a ligand herein also disclosed and further illustrated herein below. However, in accordance with the present disclosure EnSeMBLE can be used as such and/or in combination with other algorithms, methods and or applications, identifiable to the skilled person, wherein prediction of HMP structures is necessary or desired In the embodiments herein described, EnSeMBLE provides a protocol to predict not only the lowest energy structure, but also other low-energy conformations that will be relevant to understand the function of HMPs in relation to their interaction with different ligands including agonists, antagonists and inverse agonists.

A more detailed disclosure of the algorithms of the method and systems to predict HMPs structures in accordance with some embodiments of the present disclosure will now follow.

In some embodiments, prediction of the TM sequences is performed by PREDICTM. Accurate ab initio prediction of helical membrane proteins begins with the identification of the location of the transmembrane (TM) regions of the protein within the amino acid sequence.

There are many methods already available for predicting the location of TM regions. These methods encompass simple hydrophobicity-based procedures, hidden Markov models, and neural networks. Chen, Kernytsky, and Rost [9] found that hydrophobicity-based methods were less accurate than the hidden Markov models (HMM) [10] and neural network based methods, which require training or parameter fitting. Since there are very few HMP structures Applicants eschewed HMM prediction methods, was and instead developed a highly accurate hydrophobicity-based method that was simple to implement and required no input structural data (herein also indicated as ab initio), resulting in the PredicTM program.

The PredicTM algorithm in accordance with the present disclosure relies on the observation that transmembrane helices are overall hydrophobic in nature. If a hydrophobicity profile can be generated from the amino acid sequence, then the hydrophobic portions of the profile should correspond to the transmembrane helices. The present disclosure will also allow to sufficiently reducing noise without losing data.

Figure 4:
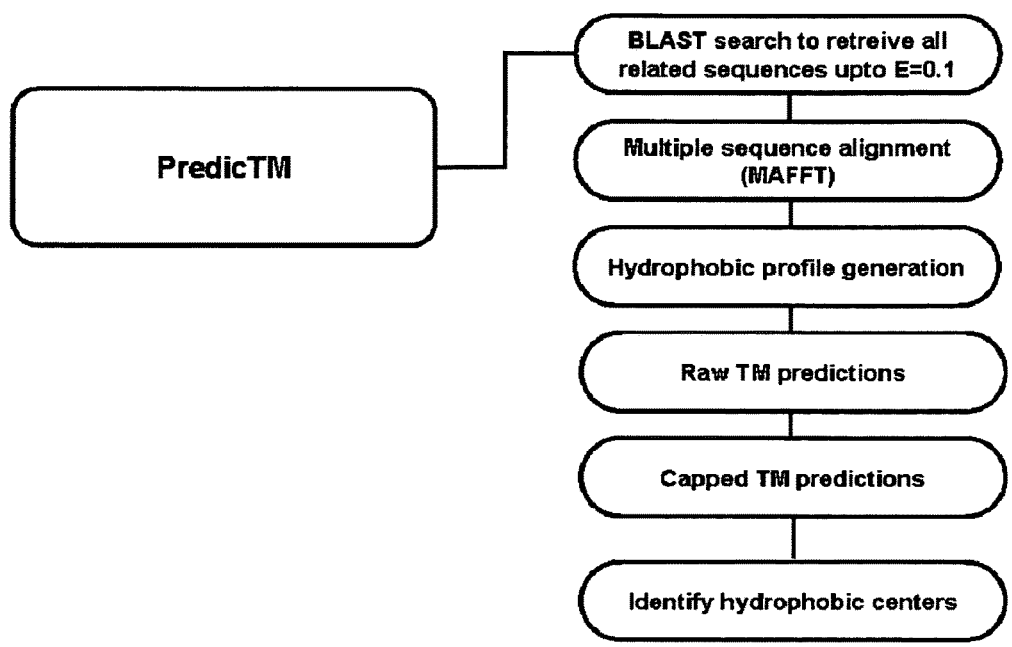
FIG. 4 shows a diagram illustrating an algorithm to predict transmembrane regions of GPCRs according to an embodiment of the present disclosure.

As shown in FIG. 4, the steps of the PredicTM procedure can be broken into six parts:
 1. Retrieval of similar protein sequences from a database
 2. Multiple sequence alignment of similar sequences
 3. Hydrophobic profile generation and noise removal
 4. Initial transmembrane region predictions
 5. Application of capping rules
 6. Identification of hydrophobic centers These six parts will now be described in detail.

Step 1: Similarity search. The first step of the procedure, retrieving sequences related to the target sequence, can be carried out through a modified BLAST search. BLAST, the Basic Local Alignment Search Tool, is a bioinformatics program used to search databases for related sequences and is widely used [11]. One of the standard implementations of BLAST, and the implementation used by PredicTM in accordance with one of the embodiments of the present disclosure, is at the Expert Protein Analysis System (ExPASy) server at the Swiss Institute of Bioinformatics (SIB).

Typically, one gives a sequence or sequence identifier as an input to a web-based form, along with some parameters, and the BLAST program will return either all sequences satisfying a statistical cutoff threshold or up to a user-specified number of sequences, whichever is reached first.

In accordance with one of the embodiments of the present disclosure, PredicTM modifies this usage somewhat. First, BLAST can be executed on the ExPASy server without using a web browser, simplifying the process for the user. Second, the goal of this step for PredicTM is to always retrieve all sequences satisfying the statistical cutoff. For this reason, PredicTM can incrementally increase the requested number of sequences until no new sequences are returned by BLAST. Once this completeness has been achieved, the sequences are returned, in FASTA format, for example, for the multiple sequence alignment step.

PredicTM can also allow the user to select some of the standard BLAST options. The ExPASy implementation of BLAST typically searches the Swiss-Prot and TrEMBL databases. However, TrEMBL is not curated and can be excluded from the searches, which is the default option for PredicTM. Additionally, the database can be restricted to a specific taxon, such as eukaryota, vertebrata, or mammalia. These options allow the user to restrict results to the most relevant species for a given protein. The E threshold is the statistical measure used by BLAST and can also be adjusted by the user. Larger E thresholds allow more loosely related proteins to appear in the results while smaller E thresholds restrict the results to more closely-related proteins. Finally, BLAST allows the user to filter sequences for regions of low complexity. These regions can often result in unrelated proteins, skewing the results. However, because nothing is known about the protein beforehand, the low-complexity filter can also mask relevant portions of the sequence and should thus be used with caution.

Step 2: Multiple sequence alignment. The second step of the PredicTM procedure is multiple sequence alignment of the sequences returned from BLAST. Previous implementations of a similar procedure used ClustalW [12] to perform this alignment, but ClustalW has been found to perform poorly, particularly if loosely related or unrelated sequences are being aligned. For example, a ClustalW alignment of the five dopamine receptors completely misaligns the sixth and seventh TM regions (TM6, TM7) of D1 and D5 due to the long third intracellular loop (IC3) of D2, D3, and D4.

In accordance with one of the embodiments of the present disclosure, the MAFFT [13] multiple sequence alignment program is used, to replace ClustalW. MAFFT has several different algorithms available, but the one that can be used by PredicTM is the "E-INS-i" method, which is best suited for sequences with multiple aligning segments separated by non-aligning segments, which perfectly describes the situation for GPCRs, 7TM proteins and HMPs in general. All GPCRs/7TM proteins have seven conserved transmembrane regions (the aligning portions) separated by non-conserved loops (the non-aligning portions). MAFFT correctly aligns all helices of the five dopamine receptors. Additionally, MAFFT does well for cases where totally unrelated sequences are introduced into the alignment. The dopamine D4 receptor has a long IC3 loop that is proline-dense. When performing a BLAST search with low-complexity filtering turned on, this loop is completely masked. When the low-complexity filter is not used, the results for a BLAST search against D4 have a large number of non-GPCR sequences. When aligned with MAFFT, these unrelated sequences typically do not align in the TM regions, thus allowing an accurate prediction to be made despite having a large number of unrelated sequences in the alignment.

FIG. 5 shows how ClustalW misaligns the five dopamine receptors. TMs 1-4 align correctly and have been left off to save space. TM5 is shown in a first color; TM6 is shown in a second color; TM7 is shown in a third color blue. Note that TM5 is aligned properly while TM6 and TM7 are not. The D1-like receptors have a shorter IC3 than the D2-like receptors but have a longer Cterminus. The result is that all of the receptors are of approximately the same length, but the location of the TMs within the sequences are different which causes ClustalW to misalign these closely related proteins. Some of the sequences of the five dopamine receptors illustrated in FIG. 5 are also indicated in the enclosed Sequence Listing from SEQ ID NO: 1 to SEQ ID NO: 30.

Figure 6:
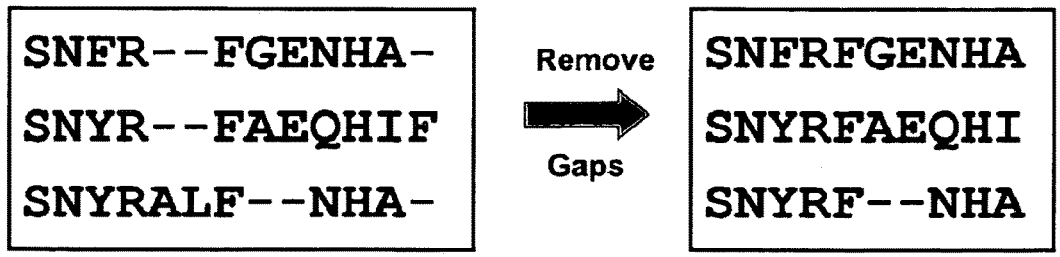
FIG. 6 shows gap removal producing a condensed alignment according to some embodiments of the present disclosure illustrated by showing exemplary sequences including the sequences identified in the enclosed sequence listing from SEQ ID NO: 31 to SEQ ID NO: 37.

Step 3: Hydrophobicity Profile. The third step of PredicTM is the generation of the hydrophobicity profile from the multiple sequence alignment. Because the sequences in the alignment typically have at least some non-aligning portions, there will almost always be gaps in the alignment of the target sequence. PredicTM is only concerned with the portions of the alignment that correspond directly to the target sequence, thus the first step of the profile generation procedure is to remove all portions of the alignment that align to gaps in the target sequence. The result is called a condensed alignment. Note that while there are no longer any gaps in the target sequence, there may still be gaps in the aligned sequences. This step is illustrated in FIG. 6 which shows sequences indicated in the enclosed Sequence Listing from SEQ ID NO: 31 to SEQ ID NO: 37.

The next sub-step is to replace the amino acids in the condensed alignment with their corresponding hydrophobicity values. PredicTM can use the Wimley-White whole-residue octanol scale [5], which is a thermodynamic scale derived from transfer of residues from water into n-octanol. Unresolved amino acids in the alignment (B, Z, J, X) are replaced with gaps rather than potentially using an incorrect hydrophobicity value.

Figure 7:
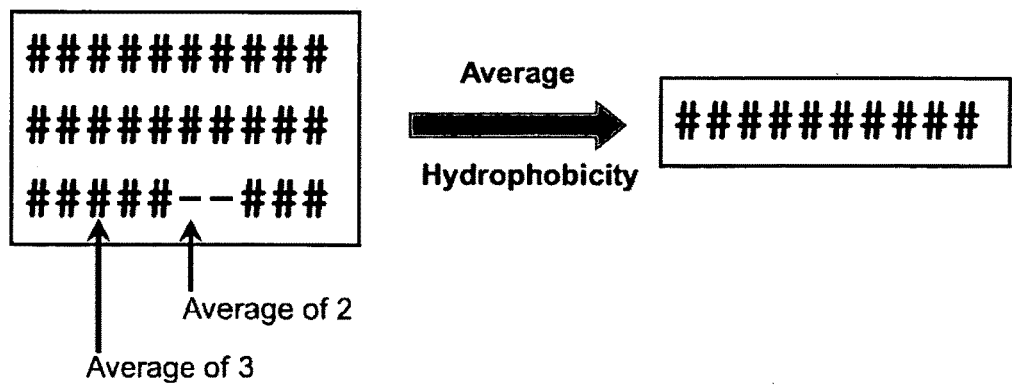
FIG. 7 shows calculation of the raw average hydrophobicity according to an embodiment of the present disclosure.

With hydrophobicity values assigned to each residue in the alignment, a raw average hydrophobicity profile is generated. This is done by taking the average of the hydrophobicity values for all non-gap residues for each position in the condensed alignment, as shown in FIG. 7. It should be noted that by removing gaps in the alignment to create the condensed alignment and by ignoring gaps when averaging hydrophobicities, PredicTM is a gap-tolerant and gap-unbiased method. The program previously used by the MSC-TM2ndS (PCT patent application WO 2005/052839 herein incorporated by reference in its entirety) was neither gap-tolerant nor gap-unbiased.

Figure 8:
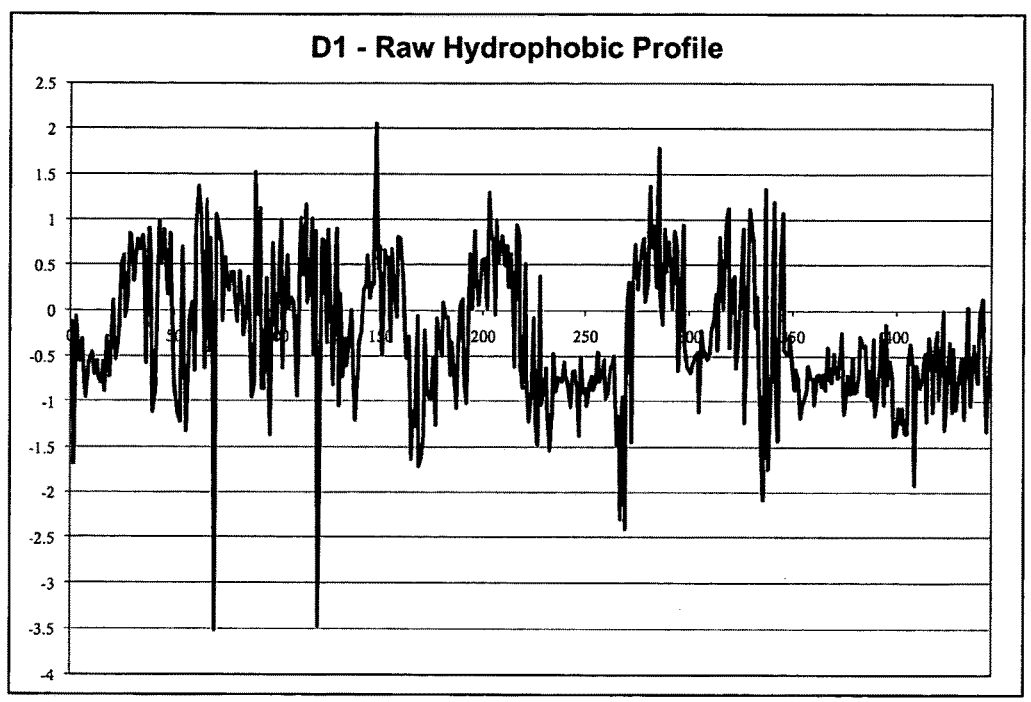
FIG. 8 shows a sample raw average hydrophobicity profile according to an embodiment of the present disclosure.

Despite this benefit that PredicTM has over previous methods, the raw average hydrophobicity can sometimes be too noisy to serve for final prediction of helices. Shown in FIG. 8 is a sample raw average hydrophobicity profile taken from a default application of PredicTM to the dopamine D1 receptor. Note that while seven peaks can be discerned, they are mostly hidden by noise. The two lowest points correspond to conserved aspartic acids in TM2 and TM3.

Figure 9:
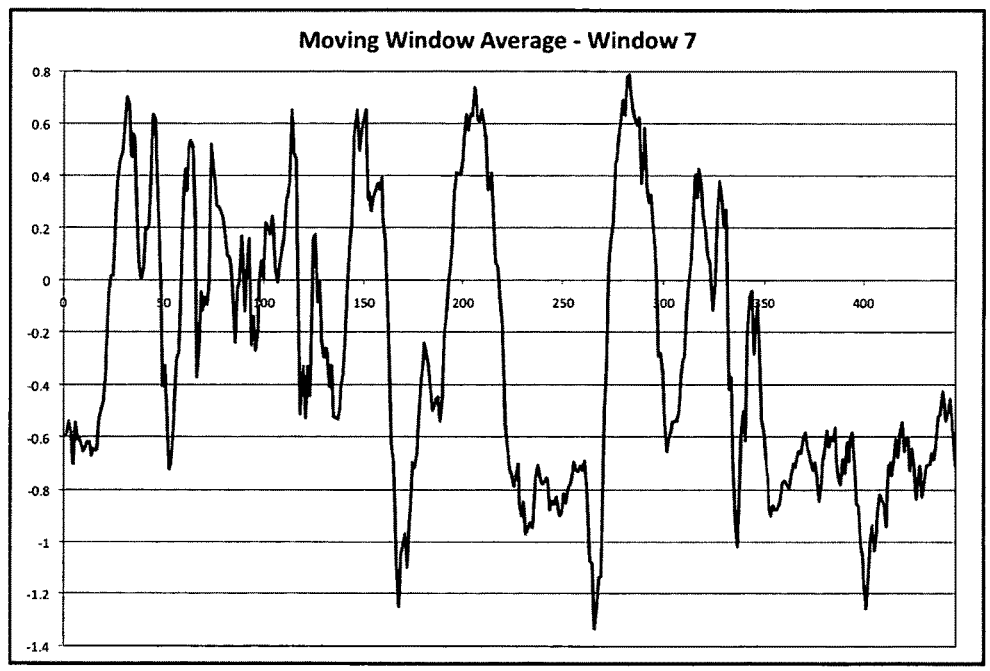
FIG. 9 shows the moving average of a window size according to an embodiment of the present disclosure.
Figure 10:
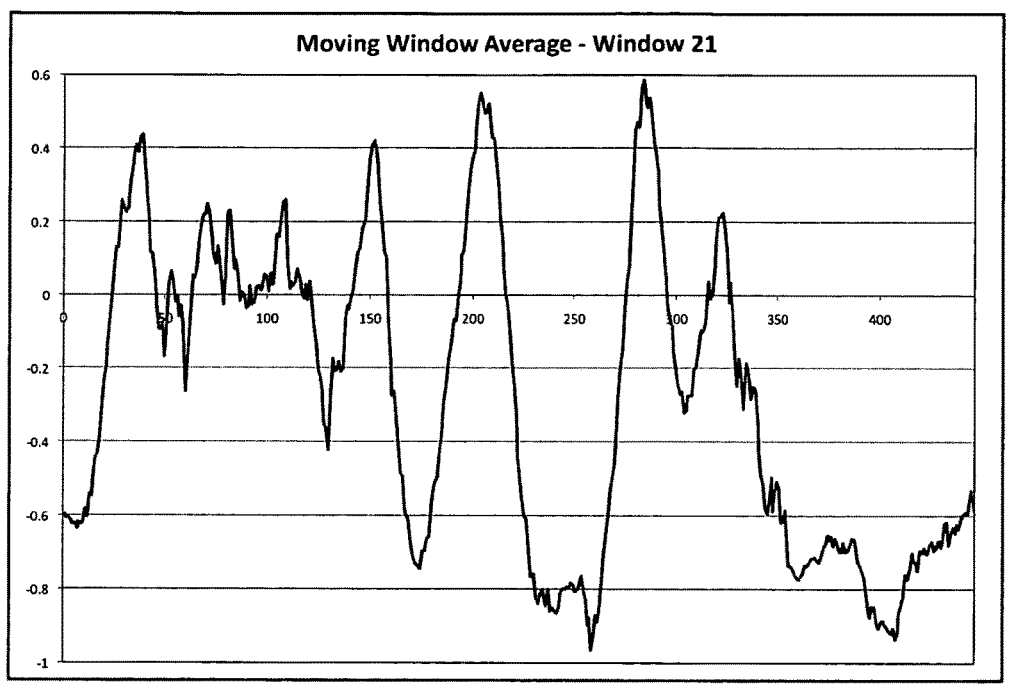
FIG. 10 shows the moving average of a window size according to an embodiment of the present disclosure.

Moving window averages can be applied to reduce the noise in the raw average profile. According to one of the embodiments of the present disclosure, the method used can be a simple moving window average without weighting. Window sizes ranging from 1 (i.e. the raw average profile) to 31 are calculated. Shown in FIGS. 9 and 10 are window sizes 7 and 21 derived from the raw average profile for D1. The peaks are much more clearly defined than in the raw average profile. However, window 7 still has a great deal of noise in TMs 1, 2, and 3 as shown by the poor resolution of TMs 1-3 in FIG. 9. Window 21 has, in contrast, significant degradation of the TM3 peak and TM3 has begun to merge with TM2 as shown by the merging of TMs 2 and 3 in FIG. 10. Prediction of TM3 is expected to be a problem for GPCRs because it is primarily an internal helix and is generally less hydrophobic in nature than the other helices. Additionally, TMs 2 and 3 and TMs 6 and 7 are often connected by very short loops, which can result in the hydrophobic peaks merging into one signal.

Figure 11:
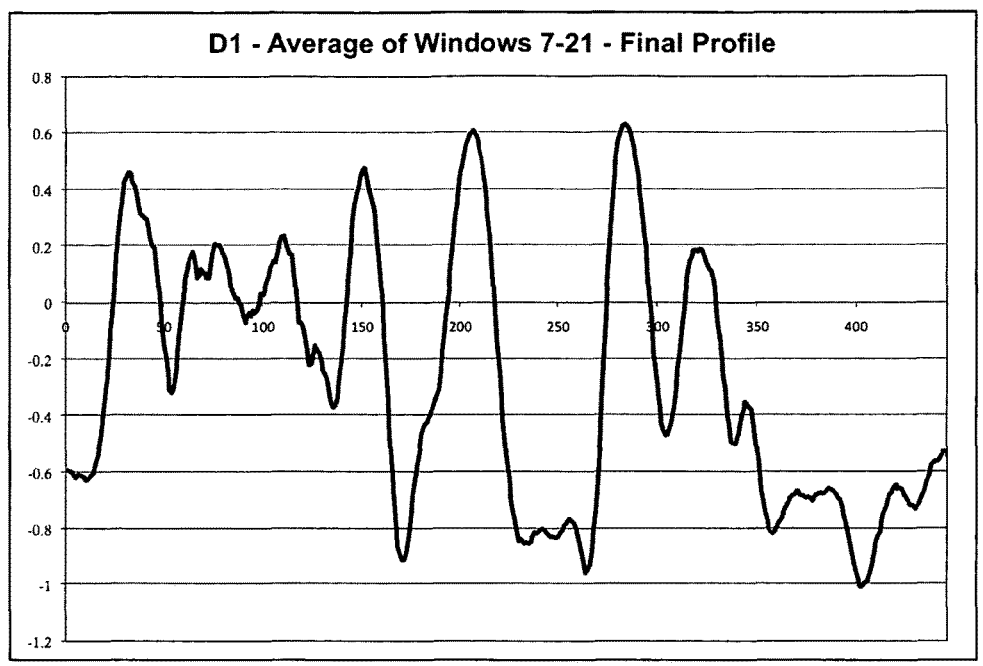
FIG. 11 shows the final profile of a protein according to an embodiment of the present disclosure.

The final sub-step in generating a hydrophobicity profile is to average the moving windows. This further reduces the noise and weights the profile by emphasizing the weight of nearby residues. In fact, a weighted moving window average could have been performed from the beginning, but that would make comparing different individual window ranges more difficult, and the current method does not require any more time than a weighted moving window average would require. The default in PredicTM is to average windows 7 through 21, with 7 corresponding to roughly one helical turn above and below a residue and 21 corresponding to roughly the length of one TM region, as shown in FIG. 11. In particular, FIG. 11 shows that TMs 1 and 4-7 are well-resolved. TMs 2 and 3 are less well resolved, but still distinct. Other averages were tested—7-31; 13-31; 7, 15, and 21—but did not perform as well when testing against the TMH Benchmark [9].

Steps 4 & 5: Initial and Capped TM Predictions. The initial prediction of helices based on the final profile is quite simple. Because a thermodynamic scale is being used, hydrophobicity values greater than zero are hydrophobic and thus are part of a transmembrane region, and values less than zero are hydrophilic and are part of the loops or termini. Typically a rule is applied that eliminates helices less than a certain length, which by default is 10 residues in PredicTM. These eliminations are noted for the user so that they can be visually inspected to ensure that they are not actually part of another helix.

Based on these initial predicted helices, termed "raw helices", capping rules are applied. First, the "helix breakers" nearest the termini (within 6 residues) of the raw helices are identified. Typical helix breakers are defined as Gly, Pro, Asp, Glu, Arg, Lys, and His. Based on the positions of the identified helix breakers, the following rules can be applied:

If a helix breaker is found for the C-term of helix i and the N-term of helix i+1:
  1. If the distance between the residues is greater than a minimum loop length (6), then apply the caps here.
  2. Otherwise, if the distance between default 4-residue extensions of both helices is greater than the minimum loop length, then apply extensions of 4 residues.
  3. Otherwise, leave the termini alone.

If a helix breaker is found for the C-term of helix i or the N-term of helix i+1:
  1. If the distance between the breaker of one helix and a default 4-residue extension of the other is greater than the minimum loop length, apply the cap and extension.
  2. Otherwise, if the distance between the breaker of one helix and the raw terminus of the other is greater than the minimum loop length, apply just the cap.
  3. Otherwise, leave the termini alone.

If helix breakers are not found for either the C-term of i or the N-term of i+1:
  1. If the distance between default 4-residue extensions of both helices is greater than the minimum loop length, then apply extensions of 4 residues.
  2. Otherwise, leave the termini alone.

Helices longer than a certain length are not eligible for capping or extensions. Also, the N-terminus of the first helix and the C-terminus of the last helix are not restricted, assuming that the helices are below the maximum length. If a breaker is found for those termini it is applied; otherwise, a default extension is applied. The reason for applying default extensions even in the absence of a helix breaker is that many transmembrane helices extend beyond the membrane [8,9]. The raw helices predicted from the hydrophobicity profile represent the core of the TM region and do not account for these common extensions beyond the membrane.

Step 6: Hydrophobic Centers. Later steps in the ab initio prediction of membrane protein structures require the orientation of helices with respect to a plane representing the center of the membrane. This requires that the center of the helix be placed on the plane. In terms of membrane protein helices, "center" is a somewhat ambiguous term. Four different hydrophobic centers are calculated for this reason. First and second are the raw midpoint ("rawmid") and capped midpoint ("capmid") centers, which correspond to the geometric center of either the raw predicted helices or the capped predicted helices. Next are the "peak" hydrophobic centers, which correspond to the residue with maximal hydrophobicity in a given TM. Finally are the "area" or "centroid" centers, which correspond to the position in the raw helix where the area of the hydrophobicity profile is equal on both sides.

Figure 12:
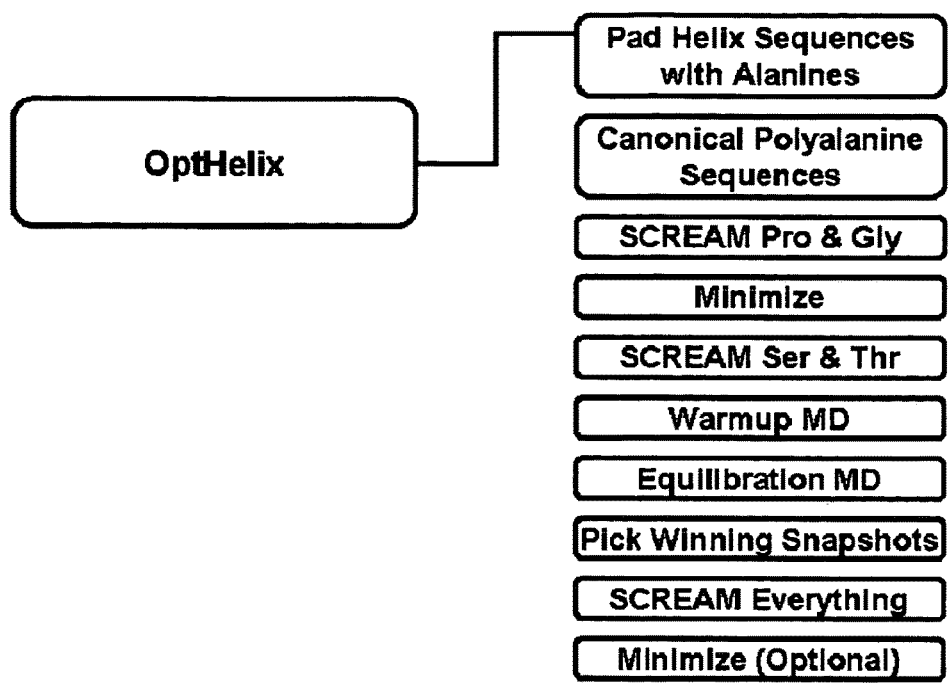
FIG. 12 shows an algorithm to optimize individual TM helices of the GPCRs according to an embodiment of the present disclosure.

In some embodiments, constructing TM helices of the HMPs is performed by OptHelix. OptHelix is a program for the optimization of transmembrane helices, particularly with respect to proline kinks. Helices are individually optimized through molecular dynamics in vacuum. According to one of the embodiments of the present disclosure, the method (shown in FIG. 12) begins by identifying the location of prolines in the TM region. When located near a terminus, these prolines can have excessively strong bending characteristics in the dynamics simulation. To alleviate this bending and to somewhat mimic the presence of the rest of the protein, alanines can be added to the terminus until the proline is 8 residues away from the terminus. As an additional option, 8 alanines can be added to the termini of all helices, regardless of proline position, or no alanines can be added. A canonical helix consisting solely of alanines is produced matching the length of the sequence. Any prolines or glycines can be placed in the helix using SCREAM (see Appendix A).

A conjugate gradient minimization, typically down to a 0.5 kcal/mol/Å RMS force threshold, can be performed on this structure. At this point, any serines or threonines can be placed on the helix using SCREAM. These residues have been shown to interact with the backbone hydrogen bonding network and can influence proline kinks [14]. The helix is now ready for molecular dynamics. Short 10 ps (5000 steps of 2 fs) dynamics runs are performed at 50K, 100K, etc. up to 250K to warm up the system. Equilibrium dynamics is performed at 300K following the warmup and is typically 2 ns in length (1,000,000 steps of 2 fs) and snapshots are taken at 10 ps intervals. Two structures are derived from the equilibrium dynamics. First, the lowest potential energy snapshot can be selected from the last 1.5 ns of the dynamics. Second, the snapshot with an RMSD closest to that of the average structure during the last 1.5 ns of dynamics can be selected. Finally, the original sidechains can be replaced using SCREAM, the structure is minimized, and any alanines that were added are removed.

Figure 14:
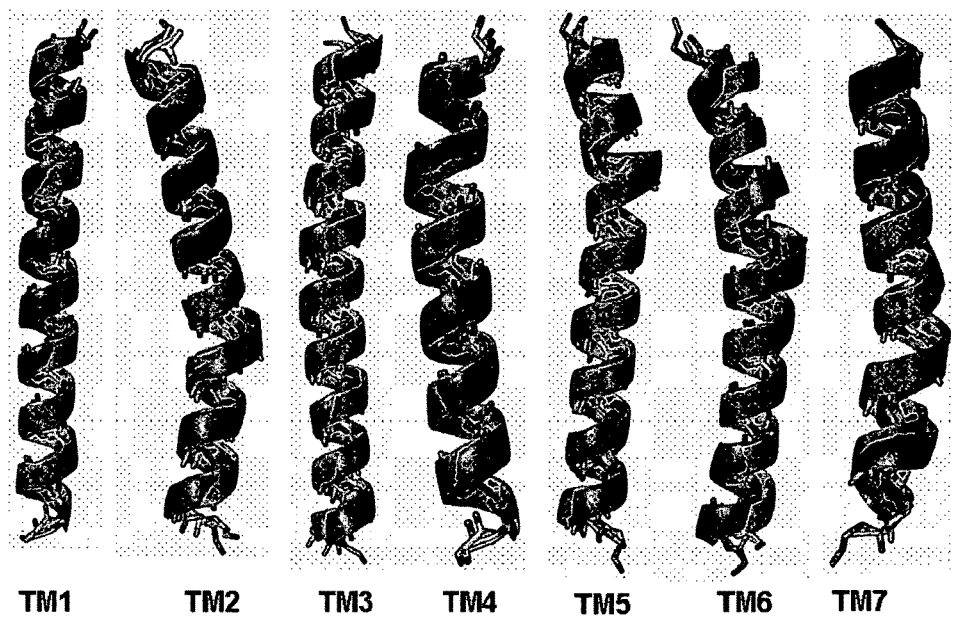
FIG. 14 shows results of the algorithm of FIG. 12, according to an embodiment of the present disclosure.

Application of OptHelix to the TMs of β2 and bovine rhodopsin yields the RMSD values shown in FIG. 13. In particular, FIG. 13 shows performance of OptHelix in terms of CRMSD measured relative to the experimental structures. Numbers are shown for two choices in OptHelix (based on RMSD to average structure and that based on best potential energy). These values are taken from only one MD run. However, all RMSD values are less than the resolution of the crystal structures [5,6] being compared to. A comparison of crystal and OptHelix helices for β2 are shown in FIG. 14. In particular, FIG. 14 shows the OptHelix results using best RMSD to average MD structure compared with crystal helices.

Figure 15:
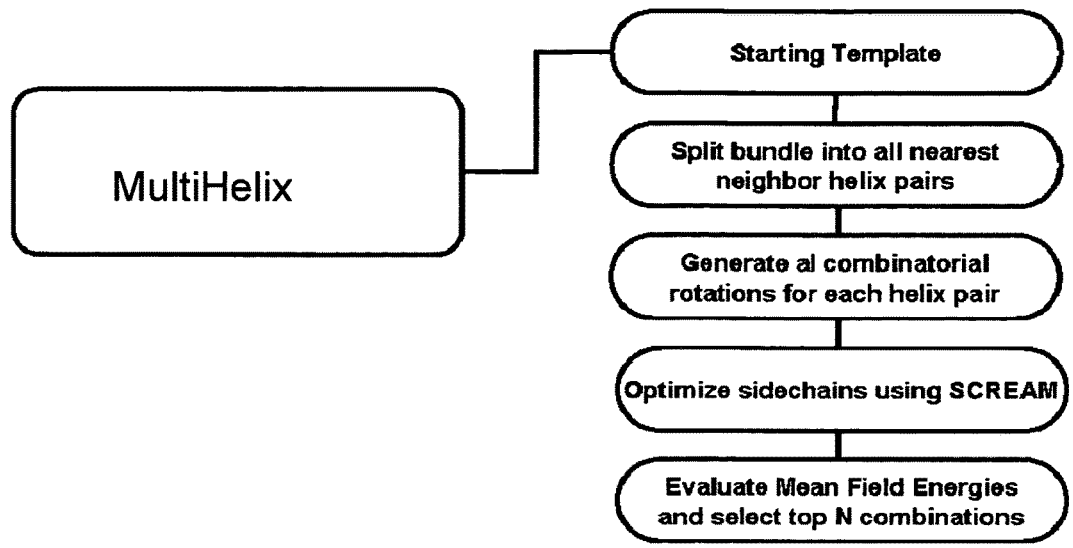
FIG. 15 shows an algorithm to perform sampling multiple conformation of GPCRs according to an embodiment herein disclosed.

In some embodiments sampling the M helices of the HMPs is performed by MULTIHELIX The steps involved in the MultiHelix procedure are shown in FIG. 15. Here is the combined description of these steps shown for the exemplary case of BiHelix (a simpler case in the MultiHelix procedure) applied to a GPCR (7-helix bundle) but applicable to all 7TM proteins and HMPs in general by way of modifications identifiable by the skilled person upon reading of the present disclosure.

In some embodiments, to identify, the starting template: pack the 7 helices from OptHelix into a bundle, which requires the definition of 6 quantities for each helix ($6*7=42$ total): the x, y, z of some reference point (like hydrophobic center from PredicTM), the tilt ($\theta$) of each axis from the z axis, the azimuthal orientation ($\varphi$) of this tilt; and the rotation ($\eta$) of the helix about the helical axis. For example, Applicants choose z=0 for the hydrophobic center (from PredicTM step) for each helix and the choice for the rotation angle $\eta$ will be described below. The remaining $4*7=28$ coordinates can be taken from a template structure.

Here are some possible choices for this template structure:
(1) the 7.5 electron density map of frog rhodopsin [15] which was used to start all our published structures.
(2) the bovine rhodopsin structure [5].
(3) the structure for the CCR1 receptor with an antagonist BX 471 bound that was subjected to 10 ns of MD using an infinite membrane and full solvent [16].
(4) the structure for the DP receptor with the CDP2 agonist bound that was subjected to 2 ns of MD using an infinite membrane and full solvent [17].
(5) the structure for the MrgC11 receptor with an agonist FdMRFa bound that was subjected to 7 ns of MD using an infinite membrane and full solvent [18].
(6) Human β2 Adrenergic Receptor [6].
(7) Any predicted but experimentally validated and well equilibrated structure.

EnSeMBLE allows for each of these templates to be used in separate predictions, providing an ensemble of bundles among which the best structures can be selected on the basis of energy or binding energy. As new structures are predicted, validated, and subjected to full MD, they will be added to the ensemble of templates.

To specify an initial rotation ($\eta$) of each helix, we use a conserved residue to match the rotation angle of its C$\alpha$ projection on the x-y plane, to that of the corresponding one in the template structure. The helical axis for rotation is defined as the one corresponding to the least moment of inertia axis obtained using all backbone atoms.

Rotational sampling of helices is then performed based on the observation that the rotation of each helix about its axis ($\eta$) is critical to defining the binding sites for ligands. This is determined by the interhelical interactions between the various residues and by the interactions with the lipid membrane as follows. A complete sampling of all helical rotational combinations, even with a 30 degree increment for each of the 7 helices, requires the sampling of $12^7$, i.e. about 35 million conformations, where the side chains need to be optimized for each helical rotation combination. This is computationally intractable and actually not necessary as in any given template some helices do not interact with each other. This led Applicants to the idea of the BiHelix sampling method described below.

In some embodiments, the MultiHelix algorithm further comprises sampling a complete set of ways to pack the M Helices of the HMPs into M-helix bundle conformations, herein also illustrated with reference to the 7 TM helices of the GPCR. In one implementation, each helix can be rotated about its axis to 12 angles (every 30 degrees) leading to a total of $12^7=35$ million conformations. (other implementations might consider more or less than 12). Evaluating all interactions between all atoms of these 35 million conformations would require an enormous computational effort, which Applicants simplify by partitioning the interactions between the 7 helices of the GPCR transmembrane region into bi-helix interactions, leading to 144 possible combinations for each of 12 important bi-helix pairs (12, 24, 45, 56, 67, 71 and 31, 32, 34, 35, 36, 37) or a total of $12*144=1728$ bi-helical cases, a relatively modest computational effort.

Figure 16:
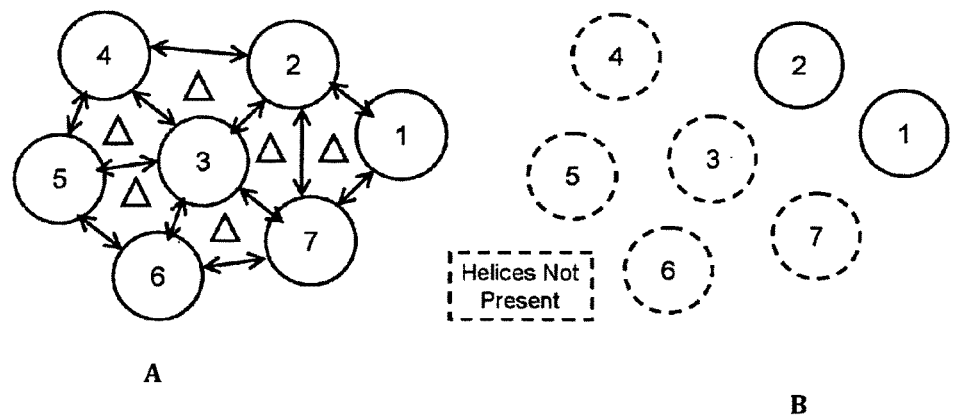
FIG. 16 shows identification of interacting pairs of helices according to an embodiment of the present disclosure. In the left panel (panel A) interacting pairs of helices with two-sided arrows are shown with triangles indicating potential three-helix interactions. In the right panel (panel B) TwoHelix rotational sampling for helix 1-2 pair is shown in the absence of other 5 helices.

In this procedure, according to one of the embodiments of the present disclosure, first interacting pairs of helices are identified based on the template being considered. The rhodopsin template for Class A GPCRs allows for 12 interacting pairs of helices (H1-H2, H1-H7, H2-H3, H2-H4, H2-H7, H3-H4, H3-H5, H3-H, H3-H7, H4-H5, H5-H6, H6-H7) as shown with two-way arrows in FIG. 16A. Now for each interacting pair of helices, Applicants sample all combinations of a full 360 degree rotation for each helix with 30 degree increments leading to $12*12=144$ combinations. During this sampling, the other 5 helices are not present, for example as shown in FIG. 16B for the helix 1-2 pair. For each rotational combination, in accordance with one of the embodiments of the present disclosure, Applicants optimize the sidechains using a new rotamer placement method, SCREAM (see Appendix A). In one of the embodiments of this procedure, only the polar sidechains can be optimized at this stage with the nonpolar/bulky sidechains (I, F, L, Y, V, W) alanized.

SCREAM uses a library of residue conformations ranging from a CRMS diversity of 0.4 A to 1.6 A in conjunction with a Monte Carlo sampling using full valence, hydrogen bond and electrostatic interactions, but special vdW potentials that reduce somewhat the penalty for contacts that are slightly too short while retaining the normal attractive interactions at full strength.

With SCREAM, Applicants have found that the selections can now be based on the total energy Escream, without separate considerations of valence, electrostatic, hydrogen bond and vdW (van der Waals). Because SCREAM does not do energy minimization, it may still lead to vdW interactions slightly too large, hence Applicants also examine the energy in which the vdW interactions of the side chains with each other and with the backbone atoms is subtracted. This is denoted as Escream-Evdw.

The original MembStruk used an algorithm called SCRWL [19], but Applicants found that it did not give very accurate interhelical interactions. As a result, Applicants found it necessary to make very small rotations (5 degree increments) and to separately examine the number of hydrogen bonds in the central regions, the number of salt bridges, and the total energies and make judgments about the best angles. This method led successfully to accurate structures but required a great deal of examination of the structures to judge which criterion was best for each case.

With SCREAM, Applicants find that rotations of 30 degrees rather than 5 can be used and obtain reliable optimum rotations. For the final best packing, local searches can be done in steps of 5 degrees to ensure that the rotation is fully optimal.

In accordance with one of the embodiments of the present disclosure, Escream and Escream-vdw energies can be taken for 144 combinations for each helix pair and use them in a pairwise addition scheme (shown for Escream):

$$e_{total}^{intra}(\eta_1, \eta_2, \eta_3, \eta_4, \eta_5, \eta_6, \eta_7) = \sum_{i=1}^{7} \frac{1}{N_i} \sum_{j=J_1}^{J_{N_i}} [e_{ij}^{i,intra}(\eta_i, \eta_j)]$$

$$e_{total}^{inter}(\eta_1, \eta_2, \eta_3, \eta_4, \eta_5, \eta_6, \eta_7) = \sum_{i=1}^{6} \sum_{j=J_1}^{J_{N_i}} [e_{ij}^{inter}(\eta_i, \eta_j)]$$

$$E^{scream}(\eta_1, \eta_2, \eta_3, \eta_4, \eta_5, \eta_6, \eta_7) = e_{tot}^{intra} + e_{tot}^{inter}$$

to obtain energies for all possible $12^7$ ~35 million conformational combinations and output the top 1000 structures with lowest Escream and Escream-Evdw energies.

As a test, Applicants applied this to procedure to Bovine Rhodopsin experimental structure (pdbid: 1u19), where Applicants removed all the loops along with the ligand retinal and only kept the experimentally determined TM helix regions. Applicants obtained the about 35 million combinations using the method mentioned above, which also samples the experimental structure that corresponds to the combination 0_0_0_0_0_0_0 (first zero corresponds to helix 1, second 0 corresponds to helix 2 and so on).

Figures 17, 18:
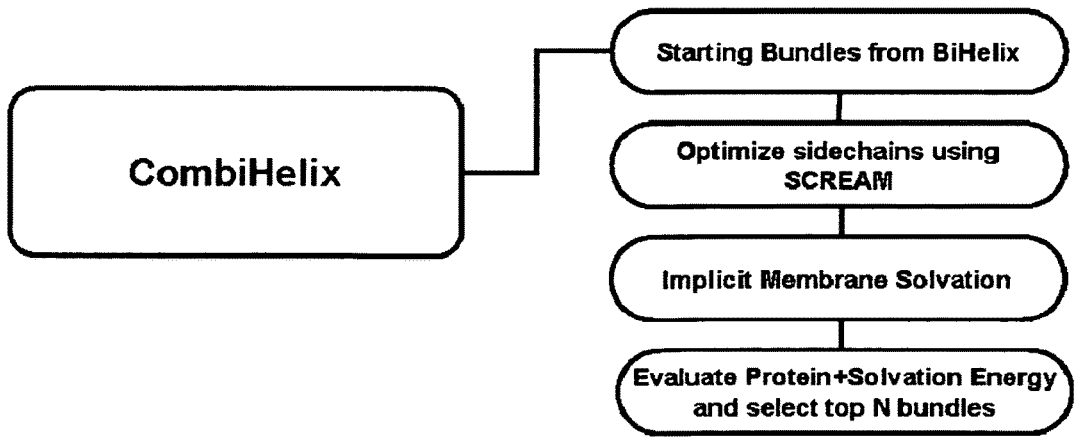
FIG. 17 shows the top 10 structures of a GPCR identified in an embodiment of the present disclosure.
FIG. 18 shows an algorithm to generate multiple rotational combinations according to some embodiments of the present disclosure.

FIG. 17 shows the top 10 structures out of about 35 million from BiHelix energy analysis for Bovine Rhodopsin. The experimental structure comes as 7th best out of that many combinations, which gives Applicants great confidence in Applicants' energy functions. Helices 1 through 4 show the crystal conformation. Helix 6 shows an alternate preference for a 30 degrees anticlockwise rotation (same as 330 clockwise rotation), which is consistent with a suggested active state of Rhodopsin, in which TM6 undergoes anticlockwise rigid-body rotation while looking at the protein from the extracellular side [20].

Helix 5 shows a surprising flexibility, but this may be due to the absence of retinal during our rotational procedure, and is actually also consistent with the putative 180 degree rotation of Helix 5 in activated Bovine Rhodopsin [21].

In some embodiments, generating multiple rotational combinations, to provide an ensemble of multiple energy structures associated to binding of the HMPs with corresponding HMP ligands is performed by COMBIHELIX. The method also comprises: using the bi-helix or multi-helix energies to estimate the total interaction energy of the full 7-helix packing for all 35 million and selecting a modest number (about 1000) for evaluation of the full interactions, a relatively modest effort. These full interaction energies are used to select the best conformations (~10 or less) that have sufficiently low energies to play role associated with binding of the HMPs with corresponding targeting compounds The steps involved in the CombiHelix procedure are shown in FIG. 18, in accordance with one of the embodiments of the present disclosure. Here is the combined description of these steps shown for a GPCR but generally applicable to any 7TM protein or HMP.

4a. Starting Bundles: The top 1000 structures coming out of BiHelix analysis can be built explicitly using the rotations specified for each helix in the combination. The helical axis for rotation can be the same as used in the BiHelix analysis.

4b. CombiHelix Bundle Optimization: For each of the bundles built in the previous step, the sidechains can be optimized using SCREAM like in the BiHelix method. The energy is reported for each bundle. In one of the embodiments of this procedure, if only the polar sidechains were optimized at the BiHelix/Multihelix step with the nonpolar/bulky sidechains (I, F, L, Y, V, W) alanized, then these nonpolar/bulky (I, F, L, Y, V, W) residues need to be dealanized using SCREAM and the energy reported for each bundle. Each bundle can also be immersed in an implicit membrane to compute membrane salvation effects that should disfavor helix rotations that expose charged residues to lipids. This membrane salvation is described in the next step.

4c. Membrane Solvation: This step evaluates protein-lipid interactions in an implicit fashion. For efficient and accurate estimation of the lipid-helix interactions, we implemented in the Delphi Poisson-Boltzmann (PB) Solver a multi-dielectric model [22] of lipid bilayers to properly take into account the penalty of exposing polar and charged residues to lipid molecules.

Figure 19:
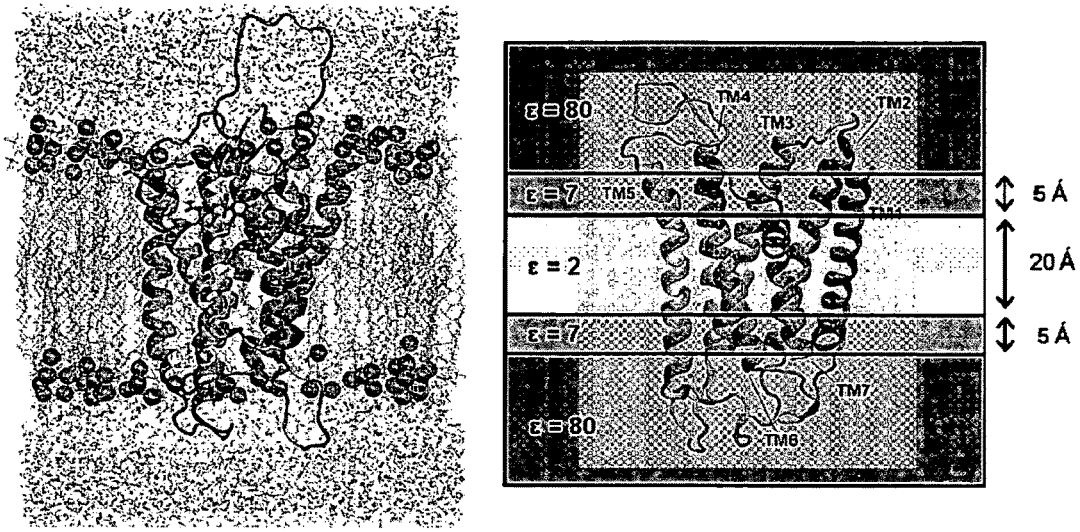
FIG. 19 shows membrane solvation models of GPCRs, and derived equation to calculate membrane salvation energy according to an embodiment of the present disclosure.

FIG. 19 shows the explicit (left) vs implicit (middle) membrane salvation model of GPCRs, and derived equation (right) to calculate membrane salvation energy As shown in FIG. 19, Applicants replace the middle 20 Angstroms of the lipid with a slab of $\in=2$, while the 5 Angstroms slabs above and below the middle slab have $\in=7$, and $\in=80$ outside the membrane. The energy of the bundle interacting with the lipid is denoted as Esolv. In addition to the PB term, a cavity term based on the White hydrophobic scale can be included. The Applicants' earlier MembStruk methods used either implicit solvent methods or a cluster of about 40 lipid molecules to mimic the membrane. In accordance with one of the embodiments of the present disclosure, for each combinatorial conformation from the BiHelix method, Applicants use the sidechain optimized structure to evaluate the membrane salvation energy Esolv and add it to the scream energy Escream from the previous step. This process leads to about 2 to 5 final structures that might play a role in differential binding of agonists, antagonists and inverse agonists to suggest possible activation pathways.

In view of the present disclosure at least the following features of EnSeMBLE will be apparent to a skilled person, upon comparison with prior art methods:
  TM Prediction: a) the search for related sequences is exhausted by going down to an E-value of 0.1; b) a thermodynamic hydrophobicity scale based on octanol is used [23]; c) MAFFT can be used instead of CLUSTALW for multiple sequence alignment. d) a gap-independent method can be used to average the hydrophobicities using a unique averaging scheme that enhances the hydrophobicity signal, minimizes the noise and due to the use of a thermodynamic hydrophobicity scale provides an unambiguous assignment of the TM regions; e) newly defined hydrophobic centers are provided (based on equal area and raw-midpoint) for each of the TM regions
  Optimization of Individual Helices: a partially alanized helix (except Pro, Ser, Thr, Gly) is used, as well as slow heating and much longer dynamics to optimize a helix.

Helix Bundle Rotational Sampling: a higher (up to 100%) sampling can be performed of all rotational combinations of TM helices is provided using a scheme that utilizes a decomposition of a helix bundle into many two-helix bundles.

In some embodiments herein disclosed, the HMP structures are used to design a HMP ligand capable of exerting a biological activity including biological activities associated with treatment of a disease.

The wording "ligand" as used herein identifies a compound able to bind a HMP so that the HMP upon binding with said compound modifies its conformation to assume a structure that is associated with a biological activity.

The wording "biological activity" as used herein indicates a process, event or series of events pertaining to the biology of the living organism where the HMP is located, such as, cellular processes by which the cell converts a biological signal to another (signal transduction), or series of biochemical reactions carried out by enzymes and resulting in signal transduction pathways. The wording "living organism" indicates an individual biological system capable to carry on the activities associated with life, which includes but is not limited to animal, plant, fungus, or micro-organisms. In at least some form, organisms are capable of reacting to stimuli, reproduction, growth and maintenance as a stable whole. An organism may be unicellular or multicellular, which include organisms, such humans, constituted by many billions of cells grouped into specialized tissues and organs. Biological activities in the sense of this disclosure also include processes involved in the regulation of intercellular communications such as communications between the cells of the immune system receptors and the series of events that constitute the inflammatory response. A further example of biological activity in the sense of this disclosure include the events associated with the autonomic nervous system transmission for both the sympathetic and parasympathetic wherein HMP biochemical pathways, responsible for control of biological activities such as blood pressure, heart rate, and digestive processes.

Exemplary ligands include ligands of the GPCRs or 7TM proteins i.e. a mobile signaling molecule that bind the receptors, such as natural ligands, agonists, antagonists and inverse agonists. The function of HMPs in general can also be affected and modulated by such ligands. The term "agonists" as used herein indicates ligands that act as signaling compounds and activate the HMPs or increase their basal activity to result in intracellular signals. The term antagonists as used herein indicates ligands that either prevent the activation of HMPs (with no basal activity) or those that prevent the binding of agonists to maintain the HMP basal biological activity unaltered. The term inverse agonists as used herein indicates ligands that decrease the basal activity of HMPs hence reducing the biological activity.

Figure 20:
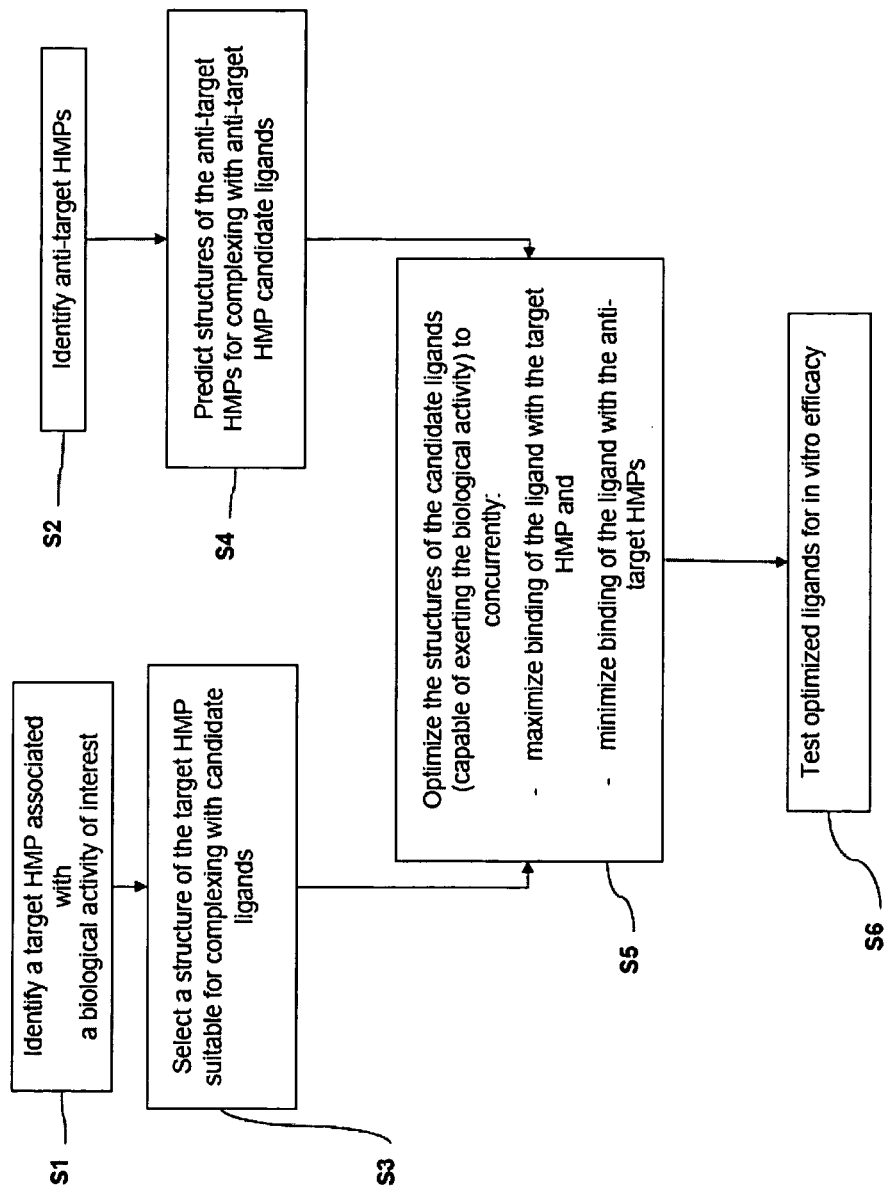
FIG. 20 shows the algorithm for performing designing a targeting compound according to an embodiment of the present disclosure.

An exemplary embodiment of the infimum approach used to design ligand able to exert a biological activity, is illustrated in FIG. 20. In the embodiment of FIG. 20, identification of target HMPs (HMPs associated with a biological activity of interest) and anti-target HMPs (HMPs related to the target HMPs through some common functional pathways and capable of cross-reacting with target HMP ligands) is performed by steps (S1) and (S2) respectively. Then structures of the HMP able to bind a candidate ligand are predicted for target HMPs (S3) and anti-target HMPs (S4). The structure of the candidate ligand is then optimized to maximize binding with the target HMPs and minimize binding with the anti-target HMPs (S5) thus providing an optimized ligand. The ability of the optimized ligand to elicit the biological activity is then verified, in particular by in vitro testing (S6).

In some embodiments herein disclosed, the "infimum" approach to design ligand is used to perform drug design (Infimum design) and the ligand can be a drug which provides its effects through binding of an HMP. The term "drug" as used herein indicates any chemical substance used in the treatment, cure, prevention, or diagnosis of disease or used to otherwise enhance physical or mental well-being.

The term "disease" as used herein indicates abnormal condition of an organism that impairs bodily functions, which is usually associated with specific symptoms and signs. In human beings, "disease" is often used more broadly to refer to any condition that causes extreme pain, dysfunction, distress, social problems, and/or death to the person afflicted, or similar problems for those in contact with the person. In this broader sense, it sometimes includes injuries, disabilities, disorders, syndromes, infections, isolated symptoms, deviant behaviors, and atypical variations of structure and function, while in other contexts and for other purposes these may be considered distinguishable categories.

In some embodiments, in the infimum approach to ligand design, the predicted structures of all HMPs (e.g. obtained from the EnSeMBLE method) are used in the design score so that the score is largest when the ligand binds strongly to one or more selected HMPs (target HMPs), while simulataneously binds very weak or does not target all other HMPs (anti-targets HMPs). Such infimum approach is in particular herein exemplified by the AntiDock algorithm further described below. The ability to design a ligand that selectively bind a predetermined HMP is particularly advantageous to design ligands for HMP such as the GPCRs since their ligands are known to cross-react (e.g. a ligand of one GPCR often binds to other GPCRs). Cross reaction in applications such as nutraceutical and pharmaceutical often leads to toxic side effects (e.g. Parkinsons vs schizophrenia for dopamine; beta 1 vs beta 2 for heart disease vs asthma).

In some embodiments of the Infimum ligand design method, the ANTIDOCK algorithm is used in combination with Steps 1 though 4 (PredicTM through CombiHelix) of EnSeMBLE which provide a practical and enabling technology to obtain the functionally relevant structural ensemble of structures of all HMPs.

This ensemble of structures for all HMPs, in turn, enables for the first time an infimum ligand design method (AntiDock) that will generate ligands suitable for activating HMPs with maximal efficacy for its target HMP, while minimizing its binding to all other HMPs. In particular in some embodiments Antidock algorithm can be used to select drug candidate molecules.

Lack of efficacy and unfavorable toxicity accounts for the failure of more than 60% of the clinical drug candidates characterized as new chemical entities (NCEs) [24]. On the other hand, the infimum-based AntiDock method will not only result in drug molecules with improved efficacy but also favorable toxicity profiles and minimal side-effects that are associated with most drugs due to their cross-reactivity.

The following steps outline the AntiDock method for such a rational ligand design process (described using a GPCR and to drug design as an example but equally applicable to any ensemble of proteins and also generally to HMP ligand design):

a) Predicting the structures of all the target GPCRs of interest, such as human GPCRs and target animal GPCRs (for preliminary testing). In this way, the structural database contains the target human GPCR, the corresponding animal GPCRs for initial experimental testing of designed drugs, and all other human GPCRs that are the anti-targets (that we don't want to hit).

b) Identify multiple scaffolds based on the target human and animal GPCR structures that will be used to identify potential lead molecules.

c) Using an automated ligand mutagenesis procedure that places different functional groups around the identified scaffolds to generate several lead molecules.

d) Dock each of the lead molecules from previous step into all GPCR structures in the database (e.g. using an algorithm such as MSCDock described later in the section) and use the database to evaluate the binding affinities of those lead compounds.

e) Optimize the scaffolds such that some of the corresponding lead molecules increase their binding affinities to target GPCRs while lowering their binding affinities to anti-target GPCRs. Existence of multiple scaffolds will maximize the chance of an ideal drug candidate that hits the target GPCRs but not the anti-target GPCRs. Scaffold optimization can be performed in a number of ways, but in our strategy we will use the highest scoring anti-target GPCR to tune the target GPCR scaffold so that it doesn't hit the highest scoring anti-target GPCR. This will be performed in an iterative way until a threshold binding energy difference is achieved between target and anti-target GPCRs for several lead molecules.

f) It is critical in the previous step to have multiple lead molecules that hit the target GPCRs and not the anti-target GPCRs because some of them may not have favorable ADMET profiles.

In the exemplary embodiments outlined in the previous paragraph, the infimum drug design can be feasible after the structures of all human GPCRs of interest are in a database. This kind of database (as well as other databases of the structures of any group of HMPs of interest) will be enabled by EnSeMBLE as all its underlying steps are very accurate and the procedure is highly efficient in terms of the time needed to obtain structures (about one every two weeks), compared to method of the art, such as MembStruk which used to take almost a whole year for one structure alone and was not successful for some of the GPCRs. Besides, this infimum-based procedure for designing drugs can eliminate the need for high-throughput screening and suggest a reasonable number of molecules that can be synthesized and tested experimentally in animal models. This infimum design is equally applicable to ligand design aimed at modulating the function of any target protein at the expense of other anti-target proteins In some embodiments of the infimum design method, docking of candidate ligand with HMPs structure can be performed by an MSCDOCK procedure or screening protocol (Docking with diversity, enrichment and protein side-chain flexibility):

The MSCDock ligand screening protocol follows a hierarchical strategy for examining ligand binding conformations and calculating their binding energies. First, the entire protein is scanned in order to find the regions most likely to bind the ligands, namely the putative binding region. Typically this leads to one or two regions, each with a volume of 1000 to 2000 Å$^3$ (a cube with sides of 10 Å to 14 Å), over which Applicants apply the following steps to predict the detailed optimal structure for the ligand-protein complex. According to one of the embodiments of the present disclosure, Applicants use a Monte Carlo method to generate various possible ligand conformations in the field of the protein. The conformations are selected based on diversity of the conformations from each other to cover the conformational space [25]. Applicants call these conformations as "family heads" and they differ from each other by at least 0.6 in CRMS (RMSD in coordinates).

Next, the energy of interaction of each family head with the protein is calculated, and about 10% of the good energy "family heads" are selected for further enrichment of these conformations. The enrichment is done by generating conformations using Monte Carlo procedure and selecting only those conformations that are close (within 0.6 CRMS) to the good energy family heads. A ligand conformation that is within 0.6 of the family head is known as a child of that family head. The enrichment cycle is performed until each chosen good energy family head has an average of at least 6 children.

Applicants then calculate the ligand protein interaction energy for all the children of each family head. The conformations (family heads and children) are sorted by energy and the best 50 ligand conformations are chosen, each of which is then taken through an optimum protein-side-chain placement using SCREAM. These structures are then conjugate-gradient minimized in two steps: first ligand-movable/protein-fixed and second all-movable. Then the binding energy is calculated for these conformations.

Software

All the steps in the EnSeMBLE method can be implemented as Perl® programs which call other underlying procedures or modules written in Perl®, Python®, C® or Fortran®. The OptHelix and BiHelix steps can be parallelized to efficiently use multiple processors. The SCREAM and MSCDock methods can be implemented as Python® programs which call other procedures or modules written in Perl®, Python®, C® or Fortran®. In principle, the EnSeMBLE, SCREAM and MSCDock methods can be written in Perl®, Python®, Ruby®, or C®. The executable steps according to the methods and algorithms of the present disclosure can be stored on a medium, a computer or on a computer readable medium.

Hardware

All the software programs were developed, tested and installed on desktop PCs and multi-node clusters with Intel processors running a Linux® operating system. OptHelix and BiHelix steps can be used in multiple-processor mode or single-processor mode. All programs should also be able to run with minimal modification on most Linux®-based PCs and clusters.

Accordingly, what has been shown are methods for predicting the ensemble of favorable three-dimensional structures for HMPs such as 7TM-like membrane proteins and their use in drug design of selective HMP ligands and in particular 7TM ligands. While these methods have been described by means of specific embodiments and applications thereof, it is understood that numerous modifications and variations could be made thereto by those skilled in the art without departing from the spirit and scope of the disclosure.

In particular, the examples set forth above are provided to give those of ordinary skill in the art a complete disclosure and description of how to make and use the embodiments of the devices, systems and methods of the disclosure, and are not intended to limit the scope of what the inventors regard as their disclosure. Modifications of the above described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually. Appendix A herein enclosed and any of the reference further cited therein is also incorporated by reference in its entirety, to the same extent as if appendix A and each reference cited therein had been incorporated by reference in its entirety individually.

Further, the paper copy of the sequence listing submitted in connection with the present application and the corresponding computer readable form are both incorporated herein by reference in their entireties.

It is to be understood that the disclosures are not limited to particular compositions or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Krogh A, Larsson B, von Heijne G, Sonnhammer EL (2001). "Predicting transmembrane protein topology with a hidden Markov model: application to complete genomes". *J. Mol. Biol.* 305, 567-580.
2. Wess J, (1999). Ed. *Structure-Function Analysis of G Protein-Coupled Receptors*, (Wiley-Liss, New York).
3. Lagerstrom M. C. and Schioth H. B. (2008) Structural diversity of G protein coupled receptors and significance for drug discovery, *Nature Reviews Drug Discovery* 7, 339-357.
4. Deisenhofer J., Epp O., Miki K., Huber R., and Michel H. 1985. Structure of the protein subunits in the photosynthetic reaction centre of Rhodospeudomonas viridis at 3 Å resolution. *Nature* 318, 618-624.
5. Palczewski, K., et al. (2000) Crystal structure of rhodopsin: A G protein-coupled receptor, *Sci.* 289, 739-745.
6. Cherezov, V., et al. (2007). "High-resolution crystal structure of an engineered human □2-adrenergic G protein-coupled receptor". *Science* 318, 1258-1265.
7. Murakami, M., Kouyama, T. (2008) Crystal structure of squid rhodopsin *Nature* 453, 363-367.
8. Kobilka B. (2007), *Biochimica et Biophysica Acta* 1768, 794-807.
9. Chen, C., A. Kernytsky, B. Rost, "Transmembrane helix predictions revisited." *Protein Science.* 11, 2774-2791 (2002).
10. Gabor Tusnády and István Simon, "The HMMTOP transmembrane topology prediction server." *Bioinformatics.* 17 (9), 849-850 (2001).
11. Altschul, S. F., et al. "Gapped BLAST and PSI-BLAST: a new generation of protein database search programs." *Nucleic Acids Res.* 25, 3389 (1997).
12. Thompson, J., D. Higgins, T. Gibson, "CLUSTAL W: improving the sensitivity of progressive multiple sequence alignment through sequence weighting, position-specific gap penalties and weight matrix choice." *Nucleic Acids Res.* 22, 4673 (1994).
13. Katoh, Kuma, Toh, Miyata, "MAFFT version 5: improvement in accuracy of multiple sequence alignment." *Nucleic Acids Res.* 33, 511 (2005).
14. Deupi, X., et al. "Ser and Thr Residues Modulate the Conformation of Pro-Kinked Transmembrane α-Helices." *Biophysical Journal.* 86, 105-115 (2004).
15. Schertler, G. F. (1998) Structure of rhodopsin. *Eye,* 12, 504-510.
16. Vaidehi, N., Schlyer, S. Trabanino, R. J., Floriano, W. B., Abrol, R., et al. (2006). Predictions of CCR1 chemokine receptor structure and BX 471 antagonist binding followed by experimental validation, *J. Biol. Chem.* 281, 27613-27620.
17. Li, Y., et al. (2007) Prediction of the 3D Structure and Dynamics of Human DP G-Protein Coupled Receptor Bound to an Agonist and an Antagonist. *J. Am. Chem. Soc.* 129, 10720-10731.
18. Heo, J., Han, S. K., Vaidehi, N., Wendel, J., Kekenes-Huskey, P., Goddard III, W. A. (2007) Prediction of the 3D Structure of FMRF-amide Neuropeptides Bound to the Mouse MrgC11 GPCR and Experimental Validation. *Chem. Bio. Chem.*, 8, 1527-1539.
19. R. L. Dunbrack Jr. and M. Karplus. "Backbone-dependent Rotamer Library for Proteins: Application to Sidechain prediction." *J. Mol. Biol.* vol. 230, 543-574 (1993).
20. Farrens D. L. et al. (1996) "Requirement of Rigid-Body Motion of Transmembrane Helices for Light Activation of Rhodopsin.", *Science* 274, 768-770.
21. E. C. Meng and H. R. Bourne, Receptor activation: what does the rhodopsin structure tell us?, *Trends Pharmacol. Sci.* 22 (2001), 587-593.
22. W. Rocchia, E. Alexov and B. Honig, Extending the applicability of the nonlinear Poisson-Boltzmann equation: Multiple dielectric constants and multivalent ions, *J. Phys. Chem. B* 105 (2001) 6507-6514.
23. Wimley W C, Creamer T P & White S H (1996). *Biochemistry* 35, 5109-5124.
24. Kubinyi H., *Nature Reviews Drug Discovery* 2, 665-668 (2003).
25. Cho, A. Wendel, J. A., Vaidehi, N., Kekenes-Huskey, P. M., Floriano, W. B., Maiti, P. K., and Goddard III, W. A. (2005) The MPSim-Dock Hierarchical Docking Algorithm: Application to the eight trypsin Inhibitor co-crystals, J. Comp. Chem., 26, 48-71.

APPENDIX A

With SCREAM, Applicants have found that the selections can now be based on the total energy Escream, without separate considerations of valence, electrostatic, hydrogen bond and vdW (van der Waals). Because SCREAM does not do energy minimization, it may still lead to vdW interactions slightly too large, hence Applicants also examine the energy in which the vdW interactions of the side chains with each other and with the backbone atoms is subtracted. This is denoted as Escream-Evdw.

SCREAM (SideChain Rotamer Energy Analysis Methodology)

A.1 Introduction

Sidechain placement methods play a major role in recent applications in the field of computational molecular biology; from protein design [A1] flexible ligand docking [A2] loop-building [A3] and to prediction of protein structures [A4]. Much attention has been paid to this important problem, which is difficult because it is in a category of problems known as NP-hard for which no efficient algorithm is known to exist. Since the groundbreaking work by Ponder and Richards [A5], many approaches have been developed, including mean-field approximation [A6], Monte Carlo algorithms [A7], and Dead-End Elimination (DEE) [A8]. In practice, however, studies have also concluded that the combinatorial issue may not be as severe as originally thought [A9]. Compared to the placement methods and rotamer libraries, scoring functions have not been studied as extensively [A10].

The scoring function in the SCREAM method is based on the all-atom forcefield DREIDING [A11] which includes an explicit hydrogen bond term. The use of a rotamer library is widely used in sidechain prediction methods, and many authors have introduced quality rotamer libraries [A12-A14] since the Ponder library [A5]. To account for the discreteness of rotamer libraries, several approaches have been introduced, such as reducing van der Waals radii [A15], capping of repulsion energy [A16], rotamer minimization [A17], and the use of subrotamer ensembles for each dominant rotamer [A18].

Applicants introduce a flat-bottom region for the van der Waals (VDW) 12-6 potential and the DREIDING hydrogen bond term (12-10 with a cosine angle term). The width of the flat-bottom depends on the specific atom of each sidechain, as well as the coarseness of the underlying rotamer library used. Applicants show that the accuracy of sidechain placement can be improved substantially by introducing the flat-bottom potential, and in a systematic way. In addition to showing that placement accuracy is dependent upon the number of rotamers used in a library, Applicants find that it is possible for suitably chosen energy functions to compensate the use of coarser rotamer libraries. Applicants demonstrate a high overall accuracy in sidechain placement, and make comparison to the popular sidechain placement program SCWRL [A19].

A.2 The Flat-Bottom Scoring Function

Figures 21, 22:
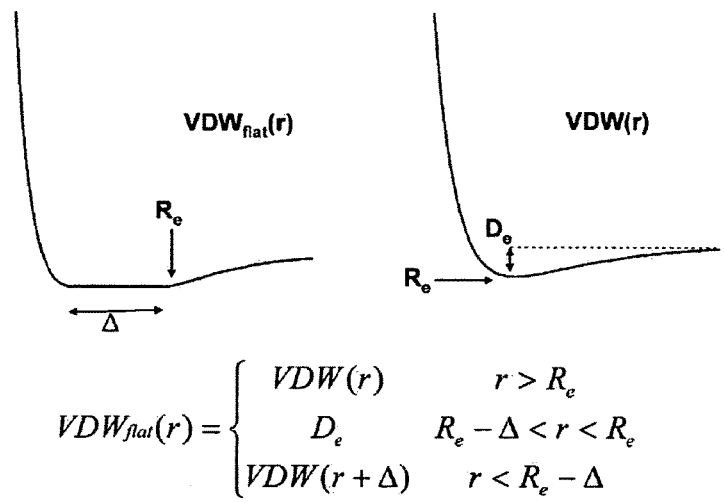
FIG. 21 shows the flat-bottom potential used in a side chain rotamer methodology according to an embodiment herein disclosed.
FIG. 22 shows the number of rotamers identified with an embodiment of the present disclosure.

Since the library is discrete, the best position for a sidechain may lead to some contacts slightly too short. Since the VDW interactions become very repulsive very quickly for distances shorter than Re, a distance too short by even 0.1 Å may cause a very repulsive VDW energy. This might lead to selecting an incorrect rotamer. In order to avoid this problem, we use a flat-bottom potential in which the attractive region is exactly the same down to Re but the repulsive region is displaced by some amount $\Delta$ so that contacts that are slightly too short by $\Delta$ will not cause a false repulsive energy. The form of this potential is shown in FIG. 21, wherein the inner wall is shifted by an amount $\Delta$.

Applicants allow a different $\Delta$ for each atom of each residue of each diversity. The way this can be done is by writing $\Delta$ as $\Delta = s \cdot \sigma$ where s is a scaling factor and the $\sigma$ is related to the range of distance deviation observed for the specific atom.

A.3 Preparation of Rotamer Libraries

Rotamer libraries of various diversities are derived from the complete coordinate rotamer library of Xiang [A9]. Applicants added hydrogens to the rotamers, and considered both $\delta$ and $\in$ versions in the case for histidines. CHARMM charges can be used throughout [A20]. Since the Xiang library was based on crystal structure data, Applicants minimized each of the conformations so that the internal energies will be consistent with subsequent energy evaluations of the proteins. To do this, Applicants placed each sidechain on a template backbone (Ala-X-Ala in the extended conformation) and did 10 steps conjugate gradient minimization using the DREIDING forcefield [A 1].

Applicants generated rotamer libraries of varying coarseness by a clustering procedure, using the heavy atom RMSD between minimized rotamers as the metric. Starting with the closest rotamers, Applicants eliminated those within the specific threshold RMSD value choosing always the rotamer with the lowest minimized DREIDING energy. This threshold RMSD value is defined as the diversity of the resulting library. To ensure that rotamers can make proper hydrogen bonds, each sidechain conformation for serine, threonine, and tyrosine was repeated with each possible polar hydrogen position. Thus, for serine and threonine, the three $sp^3$ position hydrogens were added to the hydroxyl oxygen, while for tyrosine, we add the out-of-place OH bonds 90 degrees from the phenyl ring in addition to two $sp^2$ positions in the plane. The final number of rotamers for libraries of different diversities is shown in FIG. 22.

In addition, Applicants constructed the "All-Torsion" rotamer library in which one rotamer for each major torsional angle (120 degrees for $sp^3$ anchor atoms, 180 degrees for $sp^2$ anchor atoms) was included. The angles were obtained from the backbone independent rotamer library from Dunbrack [A19] and built using the same procedure as described above. All Applicants' rotamer libraries are backbone independent.

A.4 Positioning of Sidechains

Placement of the rotamers on the backbone is decided by the coordinates of the C, C$\alpha$, N backbone atoms plus the C$\beta$ atom. To specify the position of the C$\beta$ atom, Applicants use the coordinates with respect to C, C$\alpha$, and N based on the statistics gathered from the HBPLUS protein set (see above). This involves three parameters:

1) the angle of the C$\alpha$-C$\beta$ bond from the bisector of the C-C$\alpha$-N angle: 1.81°(from the HBPLUS protein set)
2) the angle of the C$\alpha$-C$\beta$ bond with the C-C$\alpha$-N plane: 51.1° (from the HBPLUS protein set)
3) the C$\alpha$-C$\beta$ bond length: 1.55 Å (average value from the Other protein set).

Thus the C$\beta$ atom will generally have a different position from the crystal C$\beta$ position. As is common practice in the literature, Applicants did not include this C$\beta$ deviation in the RMSD calculations.

A.5 Combinatorial Placement Algorithm

According to one of the embodiments of the present disclosure, the SCREAM combinatorial placement algorithm can comprise four stages: self energy calculation for rotamers, clash elimination, and further optimization of sidechains.

Step 1: Rotamer Self Energy Calculation

The all atom forcefield DREIDING [A11] was used to calculate the interactions between atoms, with a modification to be described in the scoring function section. The internal energy contributions $E_{internal}$ (bond, angle and torsion terms and non-bonds that involve only the sidechain atoms) can be pre-calculated and stored in the rotamer library. For each residue to be replaced, the interaction energy ($E_{sc\text{-}fixed}$) can be calculated for each rotamer interacting with just the protein backbone and fixed residues (all fixed atoms). The sum of these two terms is the empty lattice energy ($E_{EL}=E_{internal}+E_{sc-fixed}$) of a rotamer in the absence of all other sidechains to be replaced. Applicants use the term ground state to refer to the rotamer with the lowest $E_{EL}$ energy. All other rotamer states are termed excited states. Excited states with an energy 50 kcal/mol above the ground state were discarded from the rotamer list for the remaining calculations.

Step 2: Clash Elimination

Eisenmenger et al. [A21] showed that the sidechain-backbone interaction accounts for the geometries of 74% of all core sidechains and 53% of all sidechains. Thus, the ground state of each sidechain was taken as the starting structure. Of course, this structure might have severe VDW clashes between sidechains since no interaction between sidechains has been included. Elimination of these clashes can be done as follows. A list of clashes of all ground state pairs, above a default threshold of 25 kcal/mol can be sorted by their clashing energies. The pair (A, B) with the worst clash can then be subjected to rotamer optimization by considering all pairs of rotamers, and selecting the lowest energy to form a super-rotamer with a new energy:

$$E_{tot}(A,B)=E_{self}(A)+E_{self}(B)+E_{Int}(A,B) \equiv E_{self}(AB)$$

where $E_{Int}$ indicates the interaction energy between rotamer A and rotamer B, which was the only energy calculation done at this step since the $E_{EL}$ terms were calculated in Stage 1.

The ground state for this super rotamer now replaced the rotamer pair in the original structure. Since large sidechains such as ARG and LYS may have as many as 700 rotamers for the 1.0 A library, Applicants limited the number of pairs to be calculated explicitly to 1,000, which we selected based upon the sum of the empty lattice energies. Of these interaction pairs, Applicants kept the ones with interaction energies below 100 kcal/mol.

After resolving a clash, Applicants considered the lowest rotamer pairs from the above calculation as a super residue. Thus, subsequent clash resolution, say between residue C and residue A, will consider interactions of all sidechains of C with the (A, B) rotamer pairs. Now the spectrum of interaction energies treats (A, B) as a super rotamer so that the (C, (A, B)) energy spectrum is treated the same as for a simple rotamer pair with the spectrum:

$$E_{tot}(A,B,C)=E_{self}(A)+E_{self}(B)+E_{self}(C)+E_{Int}(A,B)+E_{Int}(A,C)+E_{Int}(B,C)=E_{Self}(AB)+E_{self}(C)+E_{Int}(A,C)+E_{Int}(B,C) \equiv E_{Self}(AB)+E_{self}(C)+E_{Int}(AB,C)$$

This process continued by generating a new list of clashing residue pairs including the new (A, B, C), resolving the next worst clash as above. The procedure was repeated until no further clashes were identified between two rotamers or super-rotamers.

Step 3: Final Doublet Optimization

It is possible for some clashes to remain after Stage 2, since the number of rotamers pair evaluations is capped (at 1,000) and also the numbers of rotamers in a super-rotamer (20). To solve this problem, the structure from the end of stage 2 was further optimized. Sidechain pairs (termed doublets) were now ordered in decreasing energies in the presence of all other sidechains, and one iteration round of local optimization on those residue pairs was performed in that order. Any residue that had already been examined in this stage as part of a doublet was eliminated from further doublet examination. Always, the doublet with the lowest overall energy was kept.

Step 4: Final Singlet Optimizations

The structure would undergo one final round of optimization, where all residues were examined one at a time, again in order of decreasing energies for the rotamer currently placed in the structure. Again, the rotamer with the best overall energy was retained for the final structure. More iterations rounds on the final result improved the overall RMSD (unpublished results), but Applicants did not pursue this path [A22] for the purposes of this embodiment.

Applicants illustrate the effects of the doublet and singlet optimization stages by giving a specific example—1aac, using the 1.0 Å rotamer library and optimal parameters (to be described in a later section). After the clash elimination stage, the RMSD between the predicted structure and the crystal structure was 0.733 Å. The pair clashes remaining in this case included the pairs F57 and L67, V37 and F82, and V43 and W45. Doublets optimization brought the RMSD down to 0.703 Å. The final singlet optimization stage brought the RMSD value further down to 0.622 Å.

For this case, doublet optimization took 3 seconds, while singlet optimization took 13 seconds. For comparison, clash elimination took 30 seconds to complete, while the rotamer self energy calculation took 8 seconds.

A.6 Scream Performance

A.6.1 Effects of Buried vs. Exposed Residues

Figure 24:
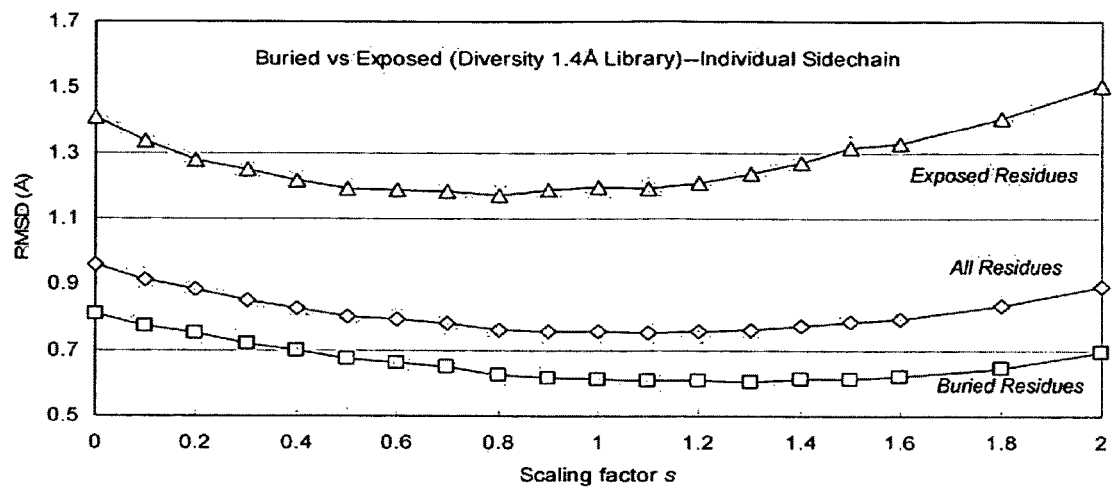
FIG. 24 shows the effects of varying the scaling factors on placement accuracies for residues according to an embodiment herein disclosed.

The percentage of exposed residues considered is only 25% because crystallographic waters and solvents were included in the calculation. Applicants consider this as the best test of the scoring function. However, in practical applications, such water and solvent molecules will not be present. This creates additional uncertainties for the surface residues whose positions should be affected by the solvent and water. Without such solvent molecules, the energy functions will tend to distort the sidechains to interact with other residues of the protein. Surface residues have more flexibility and it would be better to have smaller scaling factors for these sidechains. Thus, Applicants optimized separate scaling factors for surface residues versus bulk. To do this, Applicants calculated the SASA for the Xiang set [A13] and assigned all residues>20% exposed as surface. The resulting optimized scaling factors are in FIG. 23, wherein an accuracy comparison in single sidechain placements is shown for buried and exposed residues for the Xiang test set. FIG. 24 shows the effects of varying the scaling factors on placement accuracies for the exposed ad core residues. Shown are results from the 1.4 A diversity rotamer library results. Exposed residues account for approximately 25% of all residues. In particular, in FIG. 24, it can be seen that the accuracy for the 1.4 Å library increases from 0.809 (bulk) and 1.409 (surface) to 0.515 Å (bulk) and 1.107 Å (surface).

The current SCREAM software does not distinguish between surface and bulk residues. In order to predict the surface residues prior to assigning the sidechains, Applicants recommend using the alanized protein and rolling a ball of 2.9 Å instead of the standard 1.4 Å.

A.6.2 Placement of All Sidechains on Proteins, Comparison with SCWRL

Figure 25:
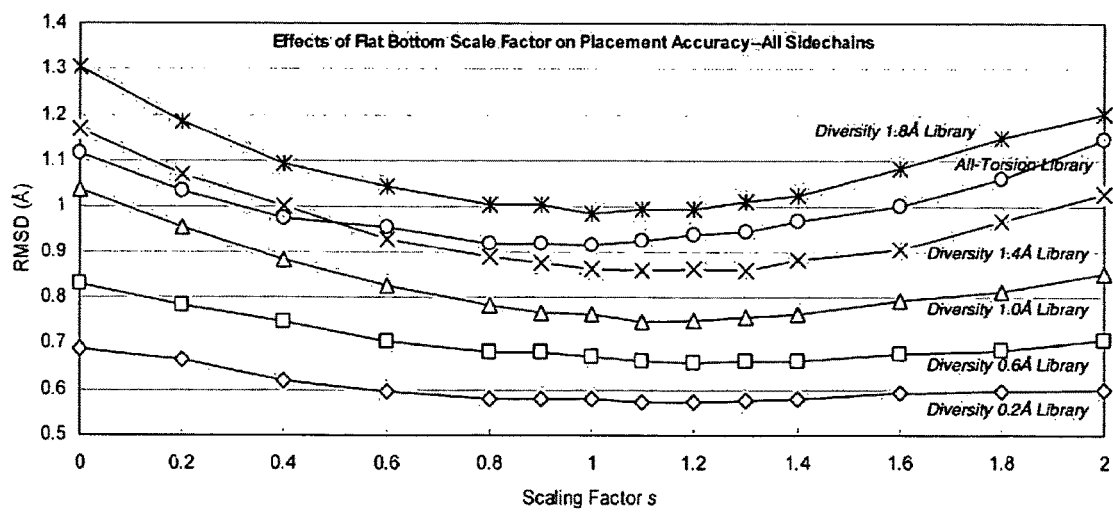
FIG. 25 shows the accuracy for simultaneously replacing all sidechains for various rotamer libraries at different s values according to some embodiments herein disclosed.

The effectiveness of the flat-bottom potential in the single-placement setting extends to multiple sidechain placements. Based on the same Xiang test set of 33 proteins, Applicants report the placement accuracy shown in FIG. 25. FIG. 25 shows the accuracy for simultaneously replacing all sidechains for various rotamer libraries at different s values. Shown are the libraries of 0.6 A (3195 rotamers), 1.0 A diversity (1014 rotamers), 1.4 A diversity (378 rotamers), 1.8 A (218 rotamers) and all-torsion (382 rotamers). The optimal s values were similar to the values from single placement tests. For example, the 1.0 Å library had an optimum scaling factor s=1.0 leading to an accuracy of 0.747 Å (compared to 0.665 Å for single placement). Overall, the accuracy discrepancy in multiple placement and single placement setting comes to a 0.09 Å RMSD. Using the χ1/χ2 criterion leads to similar conclusions.

The overall improvement in RMSD of the optimal s values over the exact Lennard-Jones potential, however, is more dramatic than in the single placement tests. For instance, by introducing the optimal s value for the float-bottom potential, in the single sidechain placement case, the accuracy improved from 0.834 Å to 0.663 Å, an improvement of 0.17 Å; in the all-sidechain placement case, the improvements went from 1.024 Å to 0.755 Å, an improvement of 0.27 Å.

To compare Applicants' results with SCWRL, Applicants applied SCWRL3.0 on the Xiang set of proteins. Applicants found an accuracy of 0.85 Å for SCWRL. A direct comparison between SCREAM and SCWRL is difficult since SCWRL uses a backbone dependent rotamer library and a more sophisticated multiple sidechain placement algorithm. However, Applicants note that the 1.8 Å SCREAM library, with just 214 rotamers, achieved an accuracy of 0.86 Å RMSD which is comparable to the 0.85 Å for SCWRL, which has a rotamer for each major torsion angle, coming to about 370 rotamers. Of course, SCWRL uses a backbone dependent rotamer library, so the specific torsion angles of those rotamers depend on the backbone φ-ψ angles.

A.8 Conclusion

SCREAM appears to represent an optimal and accurate combinatorial method for the placement of protein sidechains using a flat bottom potential. The potential is a simple modification of a Lennard-Jones potential, making it easy to incorporable into existing software.

APPENDIX REFERENCES

A1. Dwyer, M. A.; Looger, L. L.; Hellinga, H. W. *Science* 2004, 304(5679), 1967-1971.
A2. Brooijmans, N.; Kuntz, I. D. Annual Review of Biophysics and Biomolecular Structure 2003, 32, 335-373.
A3. Jacobson, M. P.; Pincus, D. L.; Rapp, C. S.; Day, T. J. F.; Honig, B.; Shaw, D. E.; Friesner, R. A. Proteins-Structure Function and Bioinformatics 2004, 55(2), 351-367.
A4. Al-Lazikani, B.; Jung, J.; Xiang, Z. X.; Honig, B. Current Opinion in Chemical Biology 2001, 5(1), 51-56.
A5. Ponder, J. W.; Richards, F. M. Journal of Molecular Biology 1987, 193(4), 775-791.
A6. Mendes, J.; Soares, C. M.; Carrondo, M. A. Biopolymers 1999, 50(2), 111-131.
A7. Kussell, E.; Shimada, J.; Shakhnovich, E. I. Journal of Molecular Biology 2001, 311(1), 183-193.
A8. Looger, L. L.; Hellinga, H. W. Journal of Molecular Biology 2001, 307(1), 429-445.
A9. Xiang, Z. X.; Honig, B. Journal of Molecular Biology 2001, 311(2), 421-430.
A10. Peterson, R. W.; Dutton, P. L.; Wand, A. J. Protein Science 2004, 13(3), 735-751.
A11. Mayo, S. L.; Olafson, B. D.; Goddard, W. A. Journal of Physical Chemistry 1990, 94(26), 8897-8909.
A12. Lovell, S. C.; Word, J. M.; Richardson, J. S.; Richardson, D. C. Proteins-Structure Function and Genetics 2000, 40(3), 389-408.
A13. Xiang, Z. X.; Honig, B. Journal of Molecular Biology 2001, 311(2), 421-430.
A14. DeMaeyer, M.; Desmet, J.; Lasters, I. Folding & Design 1997, 2(1), 53-66.
A15. Kuhlman, B.; Baker, D. Proceedings of the National Academy of Sciences of the United States of America 2000, 97(19), 10383-10388.
A16. Desjarlais, J. R.; Handel, T. M. Protein Science 1995, 4(10), 2006-2018.
A17. Wernisch, L.; Hery, S.; Wodak, S. J. Journal of Molecular Biology 2000, 301(3), 713-736.
A18. Mendes, J.; Baptista, A. M.; Carrondo, M. A.; Soares, C. M. Proteins-Structure Function and Genetics 1999, 37(4), 530-543.
A19. R. L. Dunbrack Jr. and M. Karplus. "Backbone-dependent Rotamer Library for Proteins: Application to Side-chain prediction." J. Mol. Biol. vol. 230, 543-574 (1993).
A20. MacKerell, Jr. A D, et al. (1998). "All-atom empirical potential for molecular modeling and dynamics studies of proteins". *J Phys Chem B* 102: 3586-3616.
A21. Eisenmenger, F.; Argos, P.; Abagyan, R. Journal of Molecular Biology 1993, 231(3), 849-860.
A22. Holm, L.; Sander, C. Proteins-Structure Function and Genetics 1992, 14(2), 213-223.

The invention claimed is:

1. A method for predicting protein structures of an α-helical membrane protein (HMP), the α-helical membrane protein including M α helices, M being an integer greater than or equal to 3, the method comprising:
   predicting transmembrane (TM) amino acid sequences of the HMP;
   constructing individual TM helical structures of the HMP based on said predicted TM amino acid sequences;
   defining a set of candidate M-helix bundle conformations, each conformation comprising constructed individual TM helical structures;
   partitioning interactions between the constructed individual TM helical structures of the M-helix bundle into (M−an integer)-helix sub-bundle interactions, 1≤the integer≤M−2, wherein each (M−the integer)-helix sub-bundle interaction is associated with an (M−the integer)-helix sub-bundle energy;
   estimating bundle conformation interaction energies of the defined set of candidate M-helix bundle conformations, wherein the estimating is based on a combination of all of the (M−the integer)-helix sub-bundle energies;
   based on the estimated bundle conformation interaction energies of the defined set, selecting a first subset of conformations for binding of the HMP to HMP ligands suitable to bind to the HMP;
   assembling an explicit M-helix bundle for each conformation of said first subset of conformations;
   for each said conformation of said first subset of conformations, evaluating interaction energies among all M helices;
   based on the evaluated interaction energies among all M helices, selecting a second subset of conformations, said second subset being a subset of the first subset; and
   identifying relevant HMP structures based upon binding of ligands to said second subset of conformations.

2. The method of claim 1, wherein M is 7 and the HMP is a 7 transmembrane (7 TM) protein.

3. The method of claim 2, wherein the 7 TM protein is a G protein-coupled receptor (GPCR).

4. The method of claim 1, wherein predicting the TM sequences is performed by
   predicting said TM sequences based on hydrophobicity of said TM sequences to generate a hydrophobicity profile,
wherein hydrophobic portions of the hydrophobicity profile correspond to TM helices.

5. The method of claim 1, wherein predicting the TM sequences comprises at least one between:
   a) exhausting a search for related sequences by going down to an E-value of 0.1;
   b) adopting a thermodynamic hydrophobicity scale based on octanol;
   c) adopting a multiple sequence alignment algorithm to perform multiple sequence alignment;
   d) adopting a gap-independent method to average hydrophobicities; and
   e) providing four different hydrophobic centers based on equal area, peak, cap-midpoint and raw-midpoint criteria for each of the TM sequences.

6. The method of claim 4, wherein predicting the TM regions of the HMP comprises steps of:
   performing a similarity search by retrieving protein sequences similar to sequences of the HMP from one or more databases;

performing multiple sequence alignment of the similar sequences;
generating a hydrophobic profile from the multiple sequence;
predicting an initial TM sequence;
applying capping rules; and
identifying hydrophobic centers.

7. The method of claim 6, wherein requests for the similar protein sequences from the one or more databases are incrementally increased until no new sequences are returned.

8. The method of claim 6, wherein performing the multiple sequence alignment is implemented through a multiple sequence alignment algorithm.

9. The method of claim 6, wherein generating a hydrophobic profile from the multiple sequence alignment comprises:
removing all portions of the alignment that align to gaps in the target sequence to provide a condensed alignment;
replacing the amino acids in the condensed alignment with hydrophobicity values corresponding to the amino acids; and
generating the hydrophobic profile with the hydrophobicity values assigned to each residue in the alignment.

10. The method of claim 6, further comprising removing noise after the step of generating a hydrophobic profile from the multiple sequence alignment.

11. The method of claim 10, wherein removing noise is performed through moving window averages.

12. The method of claim 6, wherein the capping rules comprise:
a first capping rule if a helix breaker is found for C-term of helix (i) and N-term of helix (i+1);
a second capping rule if a helix breaker is found for the C-term of helix (i) or the N-term of helix (i+1); and
a third capping rule if helix breakers are not found for either the C-term of helix (i) or the N-term of helix (i+1).

13. The method of claim 6, wherein the step of identifying the hydrophobic centers comprises calculation of four different hydrophobic centers.

14. The method of claim 1, wherein constructing individual TM helical structures is performed based on partially alanized helical structures.

15. The method of claim 1, wherein constructing individual TM helices comprises:
identifying location of prolines in the predicted TM sequences;
alleviating bending due to terminal prolines;
placing the located prolines in an helical structure;
performing a minimization on the helical structure thus obtained;
placing serines or threonines in the helical structure; and
performing equilibrium dynamics.

16. The method of claim 15, wherein alleviating the bending due to terminal prolines is performed by addition of alanines.

17. The method of claim 1, wherein partitioning interactions between the constructed individual TM helical structures comprises side-chain-optimization.

18. The method of claim 1, wherein defining a set of candidate M-helix bundle conformations is performed by specifying $N_i$ allowed rotation angles for each helix i in the M-helix bundle and using said rotation angles combinatorially to define $N_1*N_2*N_3* \ldots *N_M$ bundle conformations.

19. The method of claim 1, wherein partitioning interactions between the constructed individual TM helical structures comprises:
providing a starting template structure; and
determining rotation of each helical structure about its axis.

20. The method of claim 19, wherein rotation of each helix about its axis is determined by interhelical interactions between residues and by interactions with the lipid membrane.

21. The method of claim 20, wherein the interhelical interactions are obtained by:
identifying all interacting sets of (M-the integer)-helix sub-bundles;
sampling all rotational combinations of said (M-the integer)-helix bundles using the rotation angles of claim 19 up to a full 360 degree rotation for each helix; and
for each rotational combination optimizing sidechains using a sidechain placement method.

22. The method of claim 21, wherein the full 360 degree rotation is performed with 30 degree increments.

23. The method of claim 21, wherein the full 360 degree rotation is performed with increments selected from the group consisting of: 20 degrees, 15 degrees, 10 degree, and 5 degrees.

24. The method of claim 1, wherein M is greater than or equal to 3 and said interaction energies of the defined set of candidate M-helix bundle conformations are estimated by adding together
average interhelical energies for each helix interacting (M−the integer)-helix sub-bundle and
average interhelical energies for each sub-bundle.

25. The method of claim 1, wherein the first set of conformations is selected by
ordering said interaction energies and corresponding conformations in increasing order of energies; and
selecting a subset of said conformations with the lowest energies.

26. The method of claim 1, wherein assembling the explicit M-helix bundle for each conformation of said first subset of conformation comprises
identifying the rotation angle of each helix in the conformation;
rotating and placing the helix in the M-helix bundle based on a template structure; and
optimizing sidechains using a rotamer placement algorithm.

27. The method of claim 1, wherein evaluating interaction energies among all M helices comprises:
building a plurality of structures;
for each of the structures, optimizing sidechains; and
computing membrane salvation effects.

28. The method of claim 1, wherein said selecting the second subset of conformation comprises:
ordering said interaction energies and their conformations in increasing order of energies; and
selecting a subset of said ordered conformations with the lowest energies.

29. A physical computer readable medium comprising computer executable software code stored in said physical computer readable medium, which computer executable software code, upon execution, carries out the method of claim 1.

* * * * *

SEQUENCE LISTING

```
<160> NUMBER OF SEQ ID NOS: 37

<210> SEQ ID NO 1
<211> LENGTH: 12
<212> TYPE: PRT
<213> ORGANISM: Artificial Sequence
<220> FEATURE:
<223> OTHER INFORMATION: Sequence from human D1 dopamine receptor

<400> SEQUENCE: 1

Val Gln Leu Ser Trp His Lys Ala Lys Pro Thr Ser
1               5                   10

<210> SEQ ID NO 2
<211> LENGTH: 54
<212> TYPE: PRT
<213> ORGANISM: Artificial Sequence
<220> FEATURE:
<223> OTHER INFORMATION: Sequence from human D1 dopamine receptor

<400> SEQUENCE: 2
```

Pro Ser Asp Gly Asn Ala Thr Ser Leu Ala Glu Thr Ile Asp Asn Cys
1               5                   10                  15

Asp Ser Ser Leu Ser Arg Thr Tyr Ala Ile Ser Ser Val Ile Ser
            20                  25                  30

Phe Tyr Ile Pro Val Ala Ile Met Ile Val Thr Tyr Thr Arg Ile Tyr
            35                  40                  45

Arg Ile Ala Gln Lys Gln
        50

<210> SEQ ID NO 3
<211> LENGTH: 81
<212> TYPE: PRT
<213> ORGANISM: Artificial Sequence
<220> FEATURE:
<223> OTHER INFORMATION: Sequence from human D1 dopamine receptor

<400> SEQUENCE: 3

Ile Arg Arg Ile Ala Ala Leu Glu Arg Ala Ala Val His Ala Lys Asn
1               5                   10                  15

Cys Gln Thr Thr Thr Gly Asn Gly Lys Pro Val Glu Cys Ser Gln Pro
            20                  25                  30

Glu Ser Ser Phe Lys Met Ser Phe Lys Arg Glu Thr Lys Val Leu Lys
            35                  40                  45

Thr Leu Ser Val Ile Met Gly Val Phe Val Cys Cys Trp Leu Pro Phe
        50                  55                  60

Phe Ile Leu Asn Cys Ile Leu Pro Phe Cys Gly Ser Gly Glu Thr Gln
65                  70                  75                  80

Pro

<210> SEQ ID NO 4
<211> LENGTH: 68
<212> TYPE: PRT
<213> ORGANISM: Artificial Sequence
<220> FEATURE:
<223> OTHER INFORMATION: Sequence from human D1 dopamine receptor

<400> SEQUENCE: 4

Phe Cys Ile Asp Ser Asn Thr Phe Asp Val Phe Val Trp Phe Gly Trp
1               5                   10                  15

Ala Asn Ser Ser Leu Asn Pro Ile Ile Tyr Ala Phe Asn Ala Asp Phe
            20                  25                  30

Arg Lys Ala Phe Ser Thr Leu Leu Gly Cys Tyr Arg Leu Cys Pro Ala
            35                  40                  45

Thr Asn Asn Ala Ile Glu Thr Val Ser Ile Asn Asn Asn Gly Ala Ala
        50                  55                  60

Met Phe Ser Ser
65

<210> SEQ ID NO 5
<211> LENGTH: 24
<212> TYPE: PRT
<213> ORGANISM: Artificial Sequence
<220> FEATURE:
<223> OTHER INFORMATION: Sequence from human D1 dopamine receptor

<400> SEQUENCE: 5

His His Glu Pro Arg Gly Ser Ile Ser Lys Glu Cys Asn Leu Val Tyr
1               5                   10                  15

Leu Ile Pro His Ala Val Gly Ser

-continued

20

<210> SEQ ID NO 6
<211> LENGTH: 11
<212> TYPE: PRT
<213> ORGANISM: Artificial Sequence
<220> FEATURE:
<223> OTHER INFORMATION: Sequence from human D1 dopamine receptor

<400> SEQUENCE: 6

Ser Glu Asp Leu Lys Lys Glu Glu Ala Ala Gly
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Sequence from human D1 dopamine receptor

<400> SEQUENCE: 7

Ile Ala Arg Pro Leu Glu Lys Leu Ser Pro Ala Leu Ser Val Ile Leu
1               5                   10                  15

Asp Tyr Asp Thr Asp
            20

<210> SEQ ID NO 8
<211> LENGTH: 17
<212> TYPE: PRT
<213> ORGANISM: Artificial Sequence
<220> FEATURE:
<223> OTHER INFORMATION: Sequence from human D1 dopamine receptor

<400> SEQUENCE: 8

Val Ser Leu Glu Lys Ile Gln Pro Ile Thr Gln Asn Gly Gln His Pro
1               5                   10                  15

Thr

<210> SEQ ID NO 9
<211> LENGTH: 41
<212> TYPE: PRT
<213> ORGANISM: Artificial Sequence
<220> FEATURE:
<223> OTHER INFORMATION: Sequence from human D2 dopamine receptor

<400> SEQUENCE: 9

Ala Asp Gln Asn Glu Cys Ile Ile Ala Asn Pro Ala Phe Val Val Tyr
1               5                   10                  15

Ser Ser Ile Val Ser Phe Tyr Val Pro Phe Ile Val Thr Leu Leu Val
            20                  25                  30

Tyr Ile Lys Ile Tyr Ile Val Leu Arg
        35                  40

<210> SEQ ID NO 10
<211> LENGTH: 7
<212> TYPE: PRT
<213> ORGANISM: Artificial Sequence
<220> FEATURE:
<223> OTHER INFORMATION: Sequence from human D2 dopamine receptor

<400> SEQUENCE: 10

Arg Arg Arg Lys Arg Val Asn
1               5

```
<210> SEQ ID NO 11
<211> LENGTH: 137
<212> TYPE: PRT
<213> ORGANISM: Artificial Sequence
<220> FEATURE:
<223> OTHER INFORMATION: Sequence from human D2 dopamine receptor

<400> SEQUENCE: 11

Thr Lys Arg Ser Ser Arg Ala Phe Arg Ala His Leu Arg Ala Pro Leu
1               5                   10                  15

Lys Gly Asn Cys Thr His Pro Glu Asp Met Lys Leu Cys Thr Val Ile
            20                  25                  30

Met Lys Ser Asn Gly Ser Phe Pro Val Asn Arg Arg Arg Val Glu Ala
        35                  40                  45

Ala Arg Arg Ala Gln Glu Leu Glu Met Glu Met Leu Ser Ser Thr Ser
    50                  55                  60

Pro Pro Glu Arg Thr Arg Tyr Ser Pro Ile Pro Pro Ser His His Gln
65                  70                  75                  80

Leu Thr Leu Pro Asp Pro Ser His His Gly Leu His Ser Thr Pro Asp
                85                  90                  95

Ser Pro Ala Lys Pro Glu Lys Asn Gly His Ala Lys Asp His Pro Lys
            100                 105                 110

Ile Ala Lys Ile Phe Glu Ile Gln Thr Met Pro Asn Gly Lys Thr Arg
        115                 120                 125

Thr Ser Leu Lys Thr Met Ser Arg Arg
    130                 135

<210> SEQ ID NO 12
<211> LENGTH: 5
<212> TYPE: PRT
<213> ORGANISM: Artificial Sequence
<220> FEATURE:
<223> OTHER INFORMATION: Sequence from human D2 dopamine receptor

<400> SEQUENCE: 12

Lys Leu Ser Gln Gln
1               5

<210> SEQ ID NO 13
<211> LENGTH: 34
<212> TYPE: PRT
<213> ORGANISM: Artificial Sequence
<220> FEATURE:
<223> OTHER INFORMATION: Sequence from human D2 dopamine receptor

<400> SEQUENCE: 13

Lys Glu Lys Lys Ala Thr Gln Met Leu Ala Ile Val Leu Gly Val Phe
1               5                   10                  15

Ile Ile Cys Trp Leu Pro Phe Phe Ile Thr His Ile Leu Asn Ile His
            20                  25                  30

Cys Asp

<210> SEQ ID NO 14
<211> LENGTH: 43
<212> TYPE: PRT
<213> ORGANISM: Artificial Sequence
<220> FEATURE:
<223> OTHER INFORMATION: Sequence from human D2 dopamine receptor

<400> SEQUENCE: 14

Cys Asn Ile Pro Pro Val Leu Tyr Ser Ala Phe Thr Trp Leu Gly Tyr
1               5                   10                  15
```

```
Val Asn Ser Ala Val Asn Pro Ile Ile Tyr Thr Thr Phe Asn Ile Glu
                20                  25                  30

Phe Arg Lys Ala Phe Leu Lys Ile Leu His Cys
            35                  40
```

<210> SEQ ID NO 15
<211> LENGTH: 4
<212> TYPE: PRT
<213> ORGANISM: Artificial Sequence
<220> FEATURE:
<223> OTHER INFORMATION: Sequence from human D3 dopamine receptor

<400> SEQUENCE: 15

```
Phe Asn Thr Thr
1
```

<210> SEQ ID NO 16
<211> LENGTH: 42
<212> TYPE: PRT
<213> ORGANISM: Artificial Sequence
<220> FEATURE:
<223> OTHER INFORMATION: Sequence from human D3 dopamine receptor

<400> SEQUENCE: 16

```
Gly Asp Pro Thr Val Cys Ser Ile Ser Asn Pro Asp Phe Val Ile Tyr
1               5                   10                  15

Ser Ser Val Val Ser Phe Tyr Leu Pro Phe Gly Val Thr Val Leu Val
                20                  25                  30

Tyr Ala Arg Ile Tyr Val Val Leu Lys Gln
            35                  40
```

<210> SEQ ID NO 17
<211> LENGTH: 7
<212> TYPE: PRT
<213> ORGANISM: Artificial Sequence
<220> FEATURE:
<223> OTHER INFORMATION: Sequence from human D3 dopamine receptor

<400> SEQUENCE: 17

```
Arg Arg Arg Lys Arg Ile Leu
1               5
```

<210> SEQ ID NO 18
<211> LENGTH: 28
<212> TYPE: PRT
<213> ORGANISM: Artificial Sequence
<220> FEATURE:
<223> OTHER INFORMATION: Sequence from human D3 dopamine receptor

<400> SEQUENCE: 18

```
Thr Arg Gln Asn Ser Gln Cys Asn Ser Val Arg Pro Gly Phe Pro Gln
1               5                   10                  15

Gln Thr Leu Ser Pro Asp Pro Ala His Leu Glu Leu
            20                  25
```

<210> SEQ ID NO 19
<211> LENGTH: 26
<212> TYPE: PRT
<213> ORGANISM: Artificial Sequence
<220> FEATURE:
<223> OTHER INFORMATION: Sequence from human D3 dopamine receptor

<400> SEQUENCE: 19

```
Lys Arg Tyr Tyr Ser Ile Cys Gln Asp Thr Ala Leu Gly Gly Pro Gly
```

```
                 1               5                  10                 15
Phe Gln Glu Arg Gly Gly Glu Leu Lys Arg
                20              25

<210> SEQ ID NO 20
<211> LENGTH: 18
<212> TYPE: PRT
<213> ORGANISM: Artificial Sequence
<220> FEATURE:
<223> OTHER INFORMATION: Sequence from human D3 dopamine receptor

<400> SEQUENCE: 20

Glu Glu Lys Thr Arg Asn Ser Leu Ser Pro Thr Ile Ala Pro Lys Leu
1               5                  10                  15

Ser Leu

<210> SEQ ID NO 21
<211> LENGTH: 26
<212> TYPE: PRT
<213> ORGANISM: Artificial Sequence
<220> FEATURE:
<223> OTHER INFORMATION: Sequence from human D3 dopamine receptor

<400> SEQUENCE: 21

Glu Val Arg Lys Leu Ser Asn Gly Arg Leu Ser Thr Ser Leu Lys Leu
1               5                  10                  15

Gly Pro Leu Gln Pro Arg Gly Val Pro Leu
                20              25

<210> SEQ ID NO 22
<211> LENGTH: 78
<212> TYPE: PRT
<213> ORGANISM: Artificial Sequence
<220> FEATURE:
<223> OTHER INFORMATION: Sequence from human D3 dopamine receptor

<400> SEQUENCE: 22

Arg Glu Lys Lys Ala Thr Gln Met Val Ala Ile Val Leu Gly Ala Phe
1               5                  10                  15

Ile Val Cys Trp Leu Pro Phe Phe Leu Thr His Val Leu Asn Thr His
                20              25                  30

Cys Gln Thr Cys His Val Ser Pro Glu Leu Tyr Ser Ala Thr Thr Trp
            35              40                  45

Leu Gly Tyr Val Asn Ser Ala Leu Asn Pro Val Ile Tyr Thr Thr Phe
        50              55                  60

Asn Ile Glu Phe Arg Lys Ala Phe Leu Lys Ile Leu Ser Cys
65                  70                  75

<210> SEQ ID NO 23
<211> LENGTH: 92
<212> TYPE: PRT
<213> ORGANISM: Artificial Sequence
<220> FEATURE:
<223> OTHER INFORMATION: Sequence from human D4 dopamine receptor

<400> SEQUENCE: 23

Leu Asn Asp Val Arg Gly Arg Asp Pro Ala Val Cys Arg Leu Glu Asp
1               5                  10                  15

Arg Asp Tyr Val Val Tyr Ser Ser Val Cys Ser Phe Phe Leu Pro Cys
                20              25                  30

Pro Leu Met Leu Leu Leu Tyr Trp Ala Thr Phe Arg Gly Leu Gln Arg
            35              40                  45
```

Trp Glu Val Ala Arg Arg Ala Lys Leu His Gly Arg Ala Pro Arg Arg
                50                  55                  60

Pro Ser Gly Pro Gly Pro Ser Pro Thr Pro Ala Pro Arg Leu
65                  70                  75                  80

Pro Gln Asp Pro Cys Gly Pro Asp Cys Ala Pro Pro
                85                  90

<210> SEQ ID NO 24
<211> LENGTH: 202
<212> TYPE: PRT
<213> ORGANISM: Artificial Sequence
<220> FEATURE:
<223> OTHER INFORMATION: Sequence from human D4 dopamine receptor

<400> SEQUENCE: 24

Ala Pro Gly Leu Pro Arg Gly Pro Cys Gly Pro Asp Cys Ala Pro Ala
1               5                   10                  15

Ala Pro Gly Leu Pro Pro Asp Pro Cys Gly Pro Asp Cys Ala Pro Pro
                20                  25                  30

Ala Pro Gly Leu Pro Gln Asp Pro Cys Gly Pro Asp Cys Ala Pro Pro
                35                  40                  45

Ala Pro Gly Leu Pro Arg Gly Pro Cys Gly Pro Asp Cys Ala Pro Pro
            50                  55                  60

Ala Pro Gly Leu Pro Gln Asp Pro Cys Gly Pro Asp Cys Ala Pro Pro
65                  70                  75                  80

Ala Pro Gly Leu Pro Pro Asp Pro Cys Gly Ser Asn Cys Ala Pro Pro
                85                  90                  95

Asp Ala Val Arg Ala Ala Ala Leu Pro Pro Gln Thr Pro Pro Gln Thr
                100                 105                 110

Arg Arg Arg Arg Arg Ala Lys Ile Thr Gly Arg Glu Arg Lys Ala Met
                115                 120                 125

Arg Val Leu Pro Val Val Val Gly Ala Phe Leu Leu Cys Trp Thr Pro
            130                 135                 140

Phe Phe Val Val His Ile Thr Gln Ala Leu Cys Pro Ala Cys Ser Val
145                 150                 155                 160

Pro Pro Arg Leu Val Ser Ala Val Thr Trp Leu Gly Tyr Val Asn Ser
                165                 170                 175

Ala Leu Asn Pro Val Ile Tyr Thr Val Phe Asn Ala Glu Phe Arg Asn
                180                 185                 190

Val Phe Arg Lys Ala Leu Arg Ala Cys Cys
            195                 200

<210> SEQ ID NO 25
<211> LENGTH: 80
<212> TYPE: PRT
<213> ORGANISM: Artificial Sequence
<220> FEATURE:
<223> OTHER INFORMATION: Sequence from human D5 dopamine receptor

<400> SEQUENCE: 25

Val Gln Leu Asn Trp His Arg Asp Gln Ala Ala Ser Trp Gly Gly Leu
1               5                   10                  15

Asp Leu Pro Asn Asn Leu Ala Asn Trp Thr Pro Trp Glu Glu Asp Phe
                20                  25                  30

Trp Glu Pro Asp Val Asn Ala Glu Asn Cys Asp Ser Ser Leu Asn Arg
            35                  40                  45

Thr Tyr Ala Ile Ser Ser Ser Leu Ile Ser Phe Tyr Ile Pro Val Ala

```
              50                  55                  60
Ile Met Ile Val Thr Tyr Thr Arg Ile Tyr Arg Ile Ala Gln Val Gln
 65                  70                  75                  80
```

<210> SEQ ID NO 26
<211> LENGTH: 20
<212> TYPE: PRT
<213> ORGANISM: Artificial Sequence
<220> FEATURE:
<223> OTHER INFORMATION: Sequence from human D5 dopamine receptor

<400> SEQUENCE: 26

```
Ile Arg Arg Ile Ser Ser Leu Glu Arg Ala Ala Glu His Ala Gln Ser
  1               5                  10                  15

Cys Arg Ser Ser
             20
```

<210> SEQ ID NO 27
<211> LENGTH: 107
<212> TYPE: PRT
<213> ORGANISM: Artificial Sequence
<220> FEATURE:
<223> OTHER INFORMATION: Sequence from human D5 dopamine receptor

<400> SEQUENCE: 27

```
Ala Ala Cys Ala Pro Asp Thr Ser Leu Arg Ala Ser Ile Lys Lys Glu
  1               5                  10                  15

Thr Lys Val Leu Lys Thr Leu Ser Val Ile Met Gly Val Phe Val Cys
                 20                  25                  30

Cys Trp Leu Pro Phe Phe Ile Leu Asn Cys Met Val Pro Phe Cys Ser
             35                  40                  45

Gly His Pro Glu Gly Pro Pro Ala Gly Phe Pro Cys Val Ser Glu Thr
         50                  55                  60

Thr Phe Asp Val Phe Val Trp Phe Gly Trp Ala Asn Ser Ser Leu Asn
 65                  70                  75                  80

Pro Val Ile Tyr Ala Phe Asn Ala Asp Phe Gln Lys Val Phe Ala Gln
                 85                  90                  95

Leu Leu Gly Cys Ser His Phe Cys Ser Arg Thr
            100                 105
```

<210> SEQ ID NO 28
<211> LENGTH: 9
<212> TYPE: PRT
<213> ORGANISM: Artificial Sequence
<220> FEATURE:
<223> OTHER INFORMATION: Sequence from human D5 dopamine receptor

<400> SEQUENCE: 28

```
Pro Val Glu Thr Val Asn Ile Ser Asn
  1               5
```

<210> SEQ ID NO 29
<211> LENGTH: 5
<212> TYPE: PRT
<213> ORGANISM: Artificial Sequence
<220> FEATURE:
<223> OTHER INFORMATION: Sequence from human D5 dopamine receptor

<400> SEQUENCE: 29

```
Glu Leu Ile Ser Tyr
  1               5
```

```
<210> SEQ ID NO 30
<211> LENGTH: 81
<212> TYPE: PRT
<213> ORGANISM: Artificial Sequence
<220> FEATURE:
<223> OTHER INFORMATION: Sequence from human D5 dopamine receptor

<400> SEQUENCE: 30

Asn Gln Asp Ile Val Phe His Lys Glu Ile Ala Ala Tyr Ile His
1               5                   10                  15

Met Met Pro Asn Ala Val Thr Pro Gly Asn Arg Glu Val Asp Asn Asp
            20                  25                  30

Glu Glu Glu Gly Pro Phe Asp Arg Met Phe Gln Ile Tyr Gln Thr Ser
        35                  40                  45

Pro Asp Gly Asp Pro Val Ala Glu Ser Val Trp Glu Leu Asp Cys Glu
    50                  55                  60

Gly Glu Ile Ser Leu Asp Lys Ile Thr Pro Phe Thr Pro Asn Gly Phe
65                  70                  75                  80

His

<210> SEQ ID NO 31
<211> LENGTH: 4
<212> TYPE: PRT
<213> ORGANISM: Artificial Sequence
<220> FEATURE:
<223> OTHER INFORMATION: Synthetic construct

<400> SEQUENCE: 31

Ser Asn Phe Arg
1

<210> SEQ ID NO 32
<211> LENGTH: 6
<212> TYPE: PRT
<213> ORGANISM: Artificial Sequence
<220> FEATURE:
<223> OTHER INFORMATION: Synthetic construct

<400> SEQUENCE: 32

Phe Gly Glu Asn His Ala
1               5

<210> SEQ ID NO 33
<211> LENGTH: 4
<212> TYPE: PRT
<213> ORGANISM: Artificial Sequence
<220> FEATURE:
<223> OTHER INFORMATION: Synthetic construct

<400> SEQUENCE: 33

Ser Asn Tyr Arg
1

<210> SEQ ID NO 34
<211> LENGTH: 7
<212> TYPE: PRT
<213> ORGANISM: Artificial Sequence
<220> FEATURE:
<223> OTHER INFORMATION: Synthetic construct

<400> SEQUENCE: 34

Ser Asn Tyr Arg Ala Leu Phe
1               5
```

```
<210> SEQ ID NO 35
<211> LENGTH: 10
<212> TYPE: PRT
<213> ORGANISM: Artificial Sequence
<220> FEATURE:
<223> OTHER INFORMATION: Synthetic construct

<400> SEQUENCE: 35

Ser Asn Phe Arg Phe Gly Glu Asn His Ala
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic construct

<400> SEQUENCE: 36

Ser Asn Tyr Arg Phe Ala Glu Gln His Ile
1               5                   10

<210> SEQ ID NO 37
<211> LENGTH: 5
<212> TYPE: PRT
<213> ORGANISM: Artificial Sequence
<220> FEATURE:
<223> OTHER INFORMATION: Synthetic construct

<400> SEQUENCE: 37

Ser Asn Tyr Arg Phe
1               5
```